(12) United States Patent
Wang et al.

(10) Patent No.: US 12,400,737 B2
(45) Date of Patent: Aug. 26, 2025

(54) METHODS OF CLASSIFYING DIFFUSE LARGE B-CELL LYMPHOMA

(71) Applicant: CELGENE CORPORATION, Summit, NJ (US)

(72) Inventors: Yixin Wang, Basking Ridge, NJ (US); Sarah Hersey, Mendham, NJ (US); Fadi George Towfic, Madison, NJ (US); Alberto Risueno Perez, Seville (ES)

(73) Assignee: CELGENE CORPORATION, Summit, NJ (US)

( * ) Notice: Subject to any disclaimer, the term of this patent is extended or adjusted under 35 U.S.C. 154(b) by 970 days.

(21) Appl. No.: 16/597,654

(22) Filed: Oct. 9, 2019

(65) Prior Publication Data

US 2020/0118646 A1    Apr. 16, 2020

Related U.S. Application Data

(60) Provisional application No. 62/755,380, filed on Nov. 2, 2018, provisional application No. 62/744,007, filed on Oct. 10, 2018.

(51) Int. Cl.
| | | |
|---|---|---|
| *G16B 20/30* | (2019.01) | |
| *G01N 33/574* | (2006.01) | |
| *G16H 50/20* | (2018.01) | |
| *G16H 50/30* | (2018.01) | |

(52) U.S. Cl.
CPC ....... *G16B 20/30* (2019.02); *G01N 33/57407* (2013.01); *G16H 50/20* (2018.01); *G16H 50/30* (2018.01); *G01N 2333/47* (2013.01); *G01N 2333/70596* (2013.01); *G01N 2333/71* (2013.01)

(58) Field of Classification Search
CPC ..... G01N 2333/71; G01N 2333/70596; G01N 2333/47; G01N 33/57407; G01N 2800/50; G16H 50/20; G16H 50/30; G16H 10/40; G16B 20/30
See application file for complete search history.

(56) References Cited

U.S. PATENT DOCUMENTS

| | | | |
|---|---|---|---|
| 2011/0223157 A1* | 9/2011 | Schafer ............ | G01N 33/57407 435/6.12 |
| 2015/0174114 A1* | 6/2015 | Schafer .................. | A61P 35/02 506/17 |

FOREIGN PATENT DOCUMENTS

| | | | |
|---|---|---|---|
| CN | 101968491 A | * | 2/2011 |
| WO | WO 2018165142 A1 | | 9/2018 |

OTHER PUBLICATIONS

Choi, W, et al., A New Immunostain Algorithm Classifies Diffuse Large B-Cell Lymphoma into Molecular Subtypes with High Accuracy | Clinical Cancer Research | American Association for Cancer Research (aacrjournals.org) https://doi.org/10.1158/1078-0432.CCR-09-0113 (Year: 2009).*
Choi, W. W. L., et al., (A New Immunostain Algorithm Classifies Diffues Large B-cell Lymphoma into Molecular Subtypes with High Accuracy, Clin Cancer Res (2009) 15 (17): 5494-5502, https://doi.org/10.1158/1078-0432.CCR-09-0113) (Year: 2009).*
Coutinho, R., et al.,(Poor Concordance Among Nine Immunohistochemistry Classifiers of Cell-of-Origin for Diffuse Large Cell Lymphoma, doi: 10.1158/1078-0432.CCR-13-1482) (Year: 2013).*
Meyer, P.N., et al., Immunohistochemical Methods for Predicting Cell of Origin Survival in Patents with Diffuse Large B-Cell Lymphoma, J Clin Oncol. Jan. 10, 2011; 29(2): 200-207, doi: 10.1200/JCO.2010.30.0368) (Year: 2011).*
Zhang, L., et al., (Lenalidomide efficacy in activated B-cell-like subtype diffuse large B-cell lymphoma is dependent upon IRF4 and Cereblon expression, Br J Haematol Feb. 2013;160(4):487-502, doi: 10.1111/bjh.12172. Epub Dec. 18, 2012) (Year: 2012).*
Dunleavy et al (Appropriate management of molecular subtypes of diffuse large B-cell lymphoma. Oncology (Williston Park). Apr. 2014;28(4):326-34) (Year: 2014).*
Cozzolino et al., 2016, "CD10, BCL6, and MUM1 expression in diffuse large B-cell lymphoma on FNA samples," Cancer Cytopathol., 124(2):135-143 (Epub 2015).
International Searching Authority, International Search Report and Written Opinion for International Patent Application No. PCT/US2019/055376 (Pub No. WO 2020076936) mailed Dec. 30, 2019 (18 pages).
Staiger et al., 2017, "Clinical Impact of the Cell-of-Origin Classification and the MYC/ BCL2 Dual Expresser Status in Diffuse Large B-Cell Lymphoma Treated Within Prospective Clinical Trials of the German High-Grade Non-Hodgkin's Lymphoma Study Group," J. Clin. Oncol., 35(22):2515-2526 and Appendix (19 pages).
Visco et al., 2012, "Comprehensive gene expression profiling and immunohistochemical studies support application of immunophenotypic algorithm for molecular subtype classification in diffuse large B-cell lymphoma: a report from the International DLBCL Rituximab—CHOP Consortium Program Study," Leukemia, 26(9):2103-2113 and Erratum (Leukemia, 2014 28(4):980) (24 pages).

* cited by examiner

*Primary Examiner* — Gregory S Emch
*Assistant Examiner* — Ashley H. Gao
(74) *Attorney, Agent, or Firm* — Jones Day

(57) ABSTRACT

A method of predicting if a subject has an Activated B Cell-like (ABC) subtype or a non-ABC subtype of Diffuse Large B-Cell Lymphoma (DLBCL), comprising (a) obtaining a sample from the subject; (b) measuring the expression levels of CD10, MUM1, FOXP1, and optionally Bcl-6; (c) determining a composite score based on the expression levels of CD10, MUM1, and FOXP1, and optionally Bcl-6; and (d) predicting if the subject has an ABC subtype or a non-ABC subtype of DLBCL based on the composite score.

24 Claims, 19 Drawing Sheets

METHODS OF CLASSIFYING DIFFUSE LARGE B-CELL LYMPHOMA

CROSS-REFERENCE TO RELATED APPLICATIONS

This application claims the benefit of priority to U.S. Provisional Patent Application No. 62/744,007, filed Oct. 10, 2018 and U.S. Provisional Patent Application No. 62/755,380, filed Nov. 2, 2018, the disclosure of each of which is incorporated by reference herein in its entirety.

1. FIELD

Provided herein, in some embodiments, are methods of classifying and/or predicting subtypes of Diffuse Large B-Cell Lymphoma (DLBCL) using the expression levels of CD10, Bcl-6, MUM1, and FOXP1. Also provided herein, in some embodiments, are methods of selectively treating a DLBCL patient based on the expression levels of CD10, Bcl-6, MUM1, and FOXP1 in the patient.

2. BACKGROUND

The non-Hodgkin lymphomas (NHLs) are a diverse group of blood cancers that include any kind of lymphoma except Hodgkin's lymphomas. Types of NHL vary significantly in their severity, from indolent to very aggressive. Less aggressive non-Hodgkin lymphomas are compatible with a long survival while more aggressive non-Hodgkin lymphomas can be rapidly fatal without treatment. They can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. T-cell non-Hodgkin lymphomas include mycosis fungoides, anaplastic large cell lymphoma, and precursor T-lymphoblastic lymphoma. Prognosis and treatment depend on the stage and type of disease.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma.

The diffuse large B-cell lymphomas (DLBCL) can be divided into distinct molecular subtypes according to their gene profiling patterns: germinal-center B-cell-like DLBCL (GCB-DLBCL), activated B-cell-like DLBCL (ABC-DLBCL), and primary mediastinal B-cell lymphoma (PMBL) or unclassified type. These subtypes are characterized by distinct differences in survival, chemo-responsiveness, and signaling pathway dependence, particularly the NF-κB pathway. See D. Kim et al., *Journal of Clinical Oncology*, 2007 ASCO Annual Meeting Proceedings Part I. Vol 25, No. 18S (June 20 Supplement), 2007: 8082. See Bea S, et al., Blood 2005; 106: 3183-90; Ngo V. N. et al., Nature 2011; 470: 115-9. Such differences have prompted the search for more effective and subtype-specific treatment strategies in DLBCL.

In the context of DLBCL, treatment usually includes administration of a combination of chemotherapy and antibody therapy. The most widely used treatment of DLBCL is a mixture of the antibody rituximab and several chemotherapy drugs (cyclophosphamide, doxorubicin, vincristine, and prednisone (R-CHOP), and in some cases etoposide is added (R-EPOCH)). DLBCL also typically requires immediate treatment upon diagnosis due to how quickly the disease can advance. For some patients, DLBCL returns or becomes refactory following treatment. Several alternative treatments, some of which can include use of lenalidomide, are currently being tested in clinical trials for patients with newly diagnosed, relapsed or refractory DLBCL. See Czuczman M S, et al., Clin Cancer Res. 2017, 23:4127-4137.

There is a significant need for effective methods of classifying subtypes of DLBCL for administering specific treatments. The present invention satisfies this and other needs.

3. SUMMARY OF THE INVENTION

In one aspect, provided herein is a method of predicting if a subject has an Activated B Cell-like (ABC) subtype of Diffuse Large B-Cell Lymphoma (DLBCL) or a non-ABC subtype of DLBCL, comprising: (a) obtaining a sample from the subject; (b) measuring the expression levels of CD10, MUM1, FOXP1, and optionally Bcl-6 in the sample; (c) determining a composite score based on the expression levels of CD10, MUM1, FOXP1, and optionally Bcl-6; and (d) predicting if the subject has the ABC subtype of DLBCL or the non-ABC subtype of DLBCL based on the composite score. In some embodiments, the method comprises measuring the expression levels of CD10, MUM1, and FOXP1 in the sample; and determining a composite score based on the expression levels of CD10, MUM1, and FOXP1. In other embodiments, the method comprises measuring the expression levels of CD10, MUM1, FOXP1 and Bcl-6 in the sample; and determining a composite score based on the expression levels of CD10, MUM1, FOXP1 and Bcl-6.

In another aspect, provided herein is a method of treating a subject, comprising (i) predicting if the subject has an ABC or a non-ABC subtype of DLBCL using a method comprising: (a) obtaining a sample from the subject; (b) measuring the expression levels of CD10, MUM1, FOXP1, and optionally Bcl-6 in the sample; (c) determining a composite score based on the expression levels of CD10, MUM1, FOXP1, and optionally Bcl-6; and (d) predicting if the subject has the ABC subtype or the non-ABC subtype of DLBCL based on the composite score, and (ii) administering to the subject a therapeutically effective amount of a treatment compound. In some embodiments, the method comprises measuring the expression levels of CD10, MUM1, and FOXP1 in the sample; and determining a composite score based on the expression levels of CD10, MUM1, and FOXP1. In other embodiments, the method comprises measuring the expression levels of CD10, MUM1, FOXP1 and Bcl-6 in the sample; and determining a composite score based on the expression levels of CD10, MUM1, FOXP1 and Bcl-6.

In one aspect, provided herein is a method of predicting if a subject has an Activated B Cell-like (ABC) subtype of Diffuse Large B-Cell Lymphoma (DLBCL), comprising: (a) obtaining a sample from the subject; (b) measuring the expression levels of CD10, Bcl-6, MUM1, and FOXP1; (c) determining a composite score based on the expression levels of CD10, Bcl-6, MUM1, and FOXP1; and (d) predicting if the subject has an ABC subtype and/or a non-ABC subtype of DLBCL based on the composite score. In some embodiments, the method comprises predicting if the subject has an ABC subtype of DLBCL based on the composite score. In other embodiments, the method comprises predicting if the subject has a non-ABC subtype of DLBCL based on the composite score.

In another aspect, provided herein is a method of treating a subject, comprising (i) predicting if the subject has an ABC subtype of DLBCL using a method comprising: (a) obtaining a sample from the subject; (b) measuring the expression levels of CD10, Bcl-6, MUM1, and FOXP1; (c) determining a composite score based on the expression levels of CD10, Bcl-6, MUM1, and FOXP1; and (d) predicting if the subject has an ABC subtype of DLBCL based on the composite score, and (ii) administering to the subject predicted to have the ABC subtype of DLBCL a therapeutically effective amount of a compound suitable for treating the ABC subtype of DLBCL. In some specific embodiments, the compound is lenalidomide or a stereoisomer or a mixture of stereoisomers, tautomer, pharmaceutically acceptable salt, solvate, isotopologue, prodrug, hydrate, co-crystal, clathrate, or a polymorph thereof.

In some embodiments, provided herein is a method of treating a subject, comprising (i) predicting if the subject has a non-ABC subtype of DLBCL using a method comprising: (a) obtaining a sample from the subject; (b) measuring the expression levels of CD10, Bcl-6, MUM1, and FOXP1; (c) determining a composite score based on the expression levels of CD10, Bcl-6, MUM1, and FOXP1; and (d) predicting if the subject has a non-ABC subtype of DLBCL based on the composite score, and (ii) administering to the subject predicted to have the non-ABC subtype of DLBCL a therapeutically effective amount of a compound suitable for treating the non-ABC subtype of DLBCL.

In some embodiments, the subject has DLBCL. In some embodiments, the subject is a human subject.

In some embodiments, the sample is obtained from DLBCL of the subject.

In some embodiments, the expression levels of CD10, Bcl-6, MUM1, and FOXP1 are measured by an immunohistochemistry (IHC) method.

In some embodiments, the method provided herein further comprises determining (i) a first percentage, the first percentage being the percentage of the positively stained cells determined by the IHC method using an anti-CD10 antibody, (ii) a second percentage, the second percentage being the percentage of the positively stained cells determined by the IHC method using an anti-Bcl-6 antibody, (iii) a third percentage, the third percentage being the percentage of the positively stained cells determined by the IHC method using an anti-MUM1 antibody, and (iv) a fourth percentage, the fourth percentage being the percentage of the positively stained cells determined by the IHC method using an anti-FOXP1 antibody.

In some embodiments, the composite score is determined based on the following formula: composite score=−0.5×the first percentage−0.2×the second percentage+0.4×the third percentage+0.1×the fourth percentage.

In some embodiments, the method comprises predicting that the subject has the ABC subtype of DLBCL if the composite score is 8 or higher than 8.

In some embodiments, the method is used in combination with another method for predicting the subtype of DLBCL.

In another aspect, provided herein is a method of predicting if a subject has an Activated B Cell-like (ABC) subtype of Diffuse Large B-Cell Lymphoma (DLBCL), comprising: (a) obtaining a sample from the subject; (b) measuring the expression levels of CD10, MUM1, and FOXP1 in the sample; (c) determining a composite score based on the expression levels of CD10, MUM1, and FOXP1; and (d) predicting if the subject has an ABC subtype of DLBCL based on the composite score.

In yet another aspect, provided herein is a method of treating a subject, comprising (i) predicting if the subject has an ABC subtype of DLBCL using a method comprising: (a) obtaining a sample from the subject; (b) measuring the expression levels of CD10, MUM1, and FOXP1 in the sample; (c) determining a composite score based on the expression levels of CD10, MUM1, and FOXP1; and (d) predicting if the subject has an ABC subtype of DLBCL based on the composite score, and (ii) administering to the subject predicted to have the ABC subtype of DLBCL a therapeutically effective amount of lenalidomide or a stereoisomer or a mixture of stereoisomers, tautomer, pharmaceutically acceptable salt, solvate, isotopologue, prodrug, hydrate, co-crystal, clathrate, or a polymorph thereof.

In some embodiments, the subject has DLBCL. In some embodiments, the subject is a human subject.

In some embodiments, the sample is obtained from DLBCL of the subject.

In some embodiments, the expression levels of CD10, MUM1, and FOXP1 are measured by an immunohistochemistry (IHC) method.

In some embodiments, the method provided herein further comprises determining (i) a first percentage, the first percentage being the percentage of the positively stained cells determined by the IHC method using an anti-CD10 antibody, (ii) a second percentage, the second percentage being the percentage of the positively stained cells determined by the IHC method using an anti-MUM1 antibody, and (iii) a third percentage, the third percentage being the percentage of the positively stained cells determined by the IHC method using an anti-FOXP1 antibody.

In some embodiments, the composite score is determined based on the following formula: composite score=−1.4367173−0.0238081×the first percentage+0.01051371×the second percentage+0.02111138×the third percentage.

In some embodiments, the method comprises predicting that the subject has the ABC subtype of DLBCL if the composite score is 0 or higher than 0.

In some embodiments, the method is used in combination with a second method for predicting if the subject has the ABC subtype of DLBCL.

In yet another aspect, provided herein is a method of predicting if a subject has a non-Activated B Cell-like (ABC) subtype of Diffuse Large B-Cell Lymphoma (DLBCL), comprising: (a) obtaining a sample from the subject; (b) measuring the expression levels of CD10, MUM1, and FOXP1 in the sample; (c) determining a composite score based on the expression levels of CD10, MUM1, and FOXP1; and (d) predicting if the subject has the non-ABC subtype of DLBCL based on the composite score.

In yet another aspect, provided herein is a method of treating a subject, comprising (i) predicting if the subject has a non-ABC subtype of DLBCL using a method comprising: (a) obtaining a sample from the subject; (b) measuring the expression levels of CD10, MUM1, and FOXP1 in the sample; (c) determining a composite score based on the expression levels of CD10, MUM1, and FOXP1; and (d) predicting if the subject has the non-ABC subtype of DLBCL based on the composite score, and (ii) administering to the subject predicted to have the non-ABC subtype of DLBCL a therapeutically effective amount of a treatment compound.

In some embodiments, the subject has DLBCL. In some embodiments, the subject is a human subject.

In some embodiments, the sample is obtained from DLBCL of the subject.

In some embodiments, the expression levels of CD10, MUM1, and FOXP1 are measured by an immunohistochemistry (IHC) method.

In some embodiments, the method further comprises determining (i) a first percentage, the first percentage being the percentage of the positively stained cells determined by the IHC method using an anti-CD10 antibody, (ii) a second percentage, the second percentage being the percentage of the positively stained cells determined by the IHC method using an anti-MUM1 antibody, and (iii) a third percentage, the third percentage being the percentage of the positively stained cells determined by the IHC method using an anti-FOXP1 antibody.

In some embodiments, the composite score is determined based on the following formula: composite score=−1.4367173−0.0238081×the first percentage+0.01051371×the second percentage+0.02111138×the third percentage.

In some embodiments, the method provided herein comprises predicting that the subject has the non-ABC subtype of DLBCL if the composite score is lower than 0.

In some embodiments, the method is used in combination with a second method for predicting if the subject has the non-ABC subtype of DLBCL.

4. BRIEF DESCRIPTION OF THE FIGURES

Figure 3A:
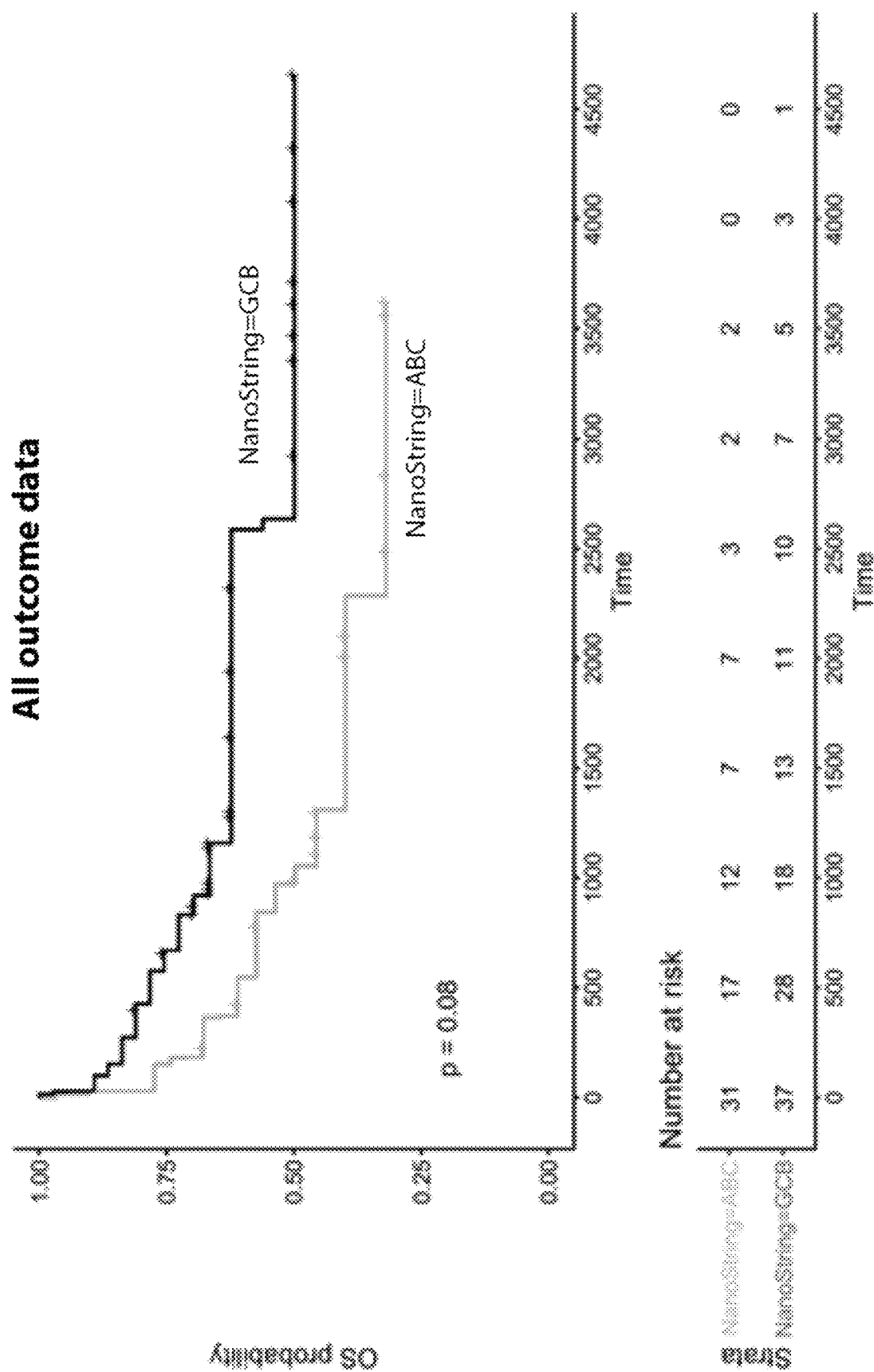
Figure 3B:
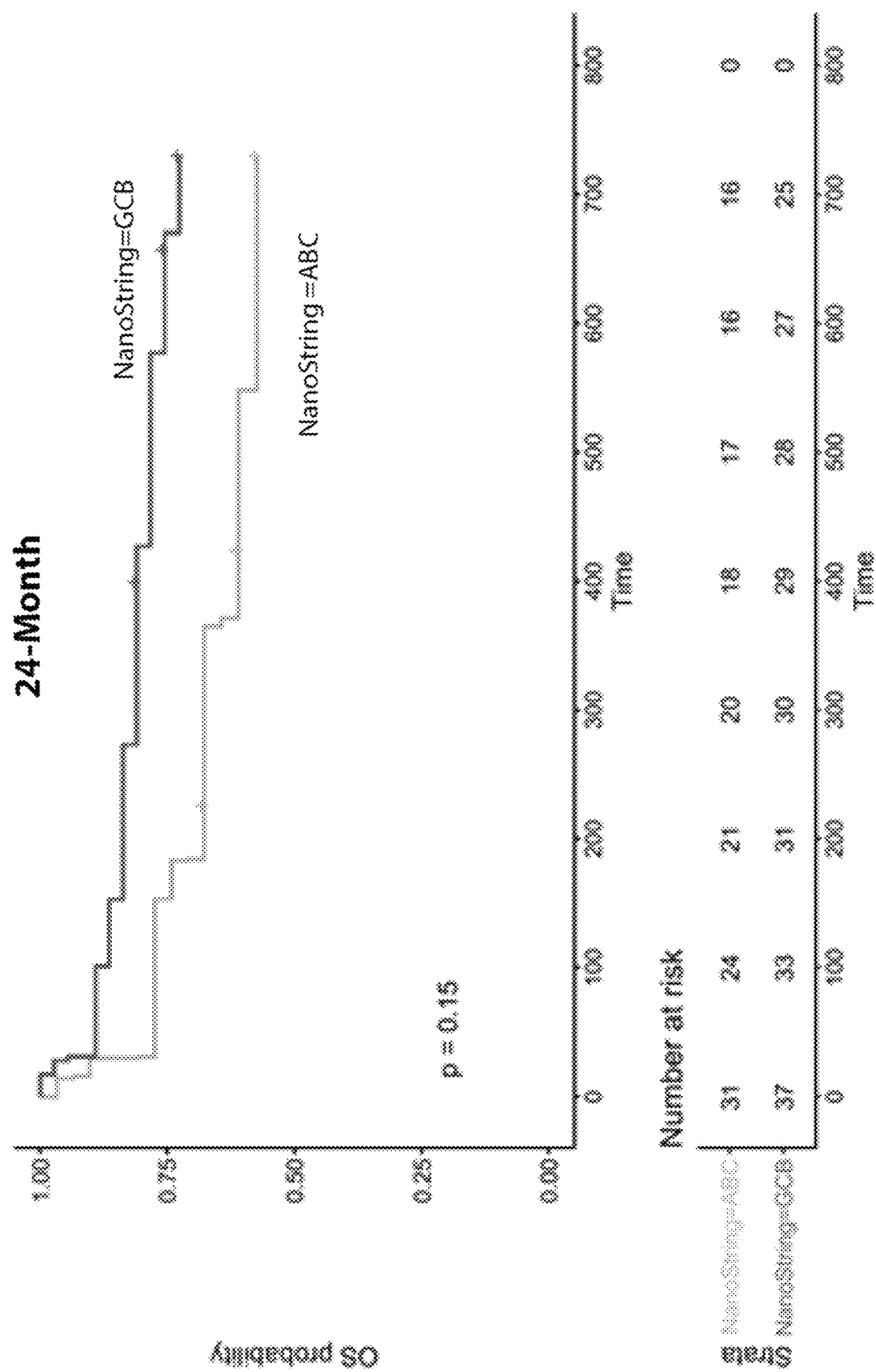
Figure 3C:
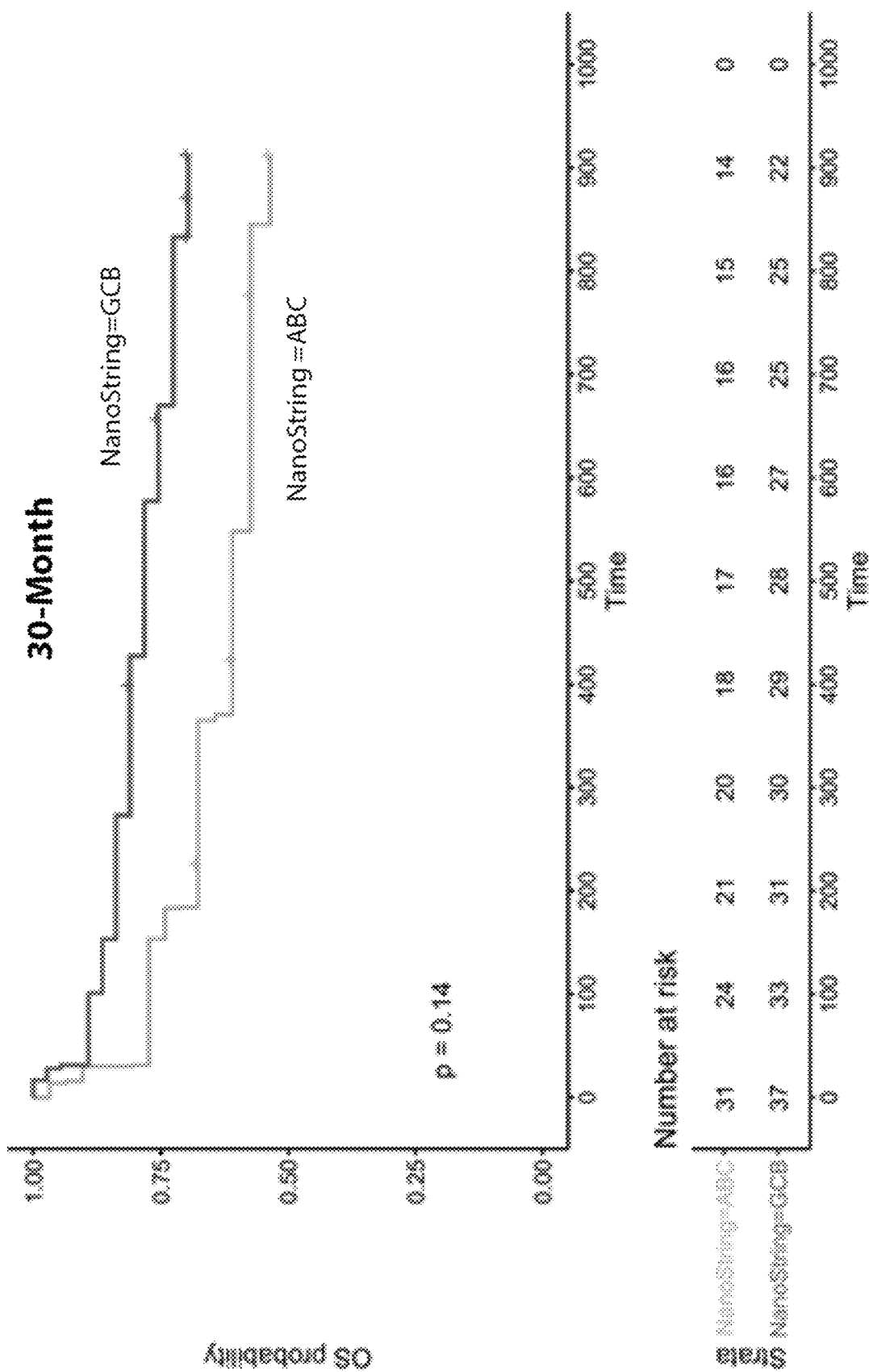
Figure 3D:
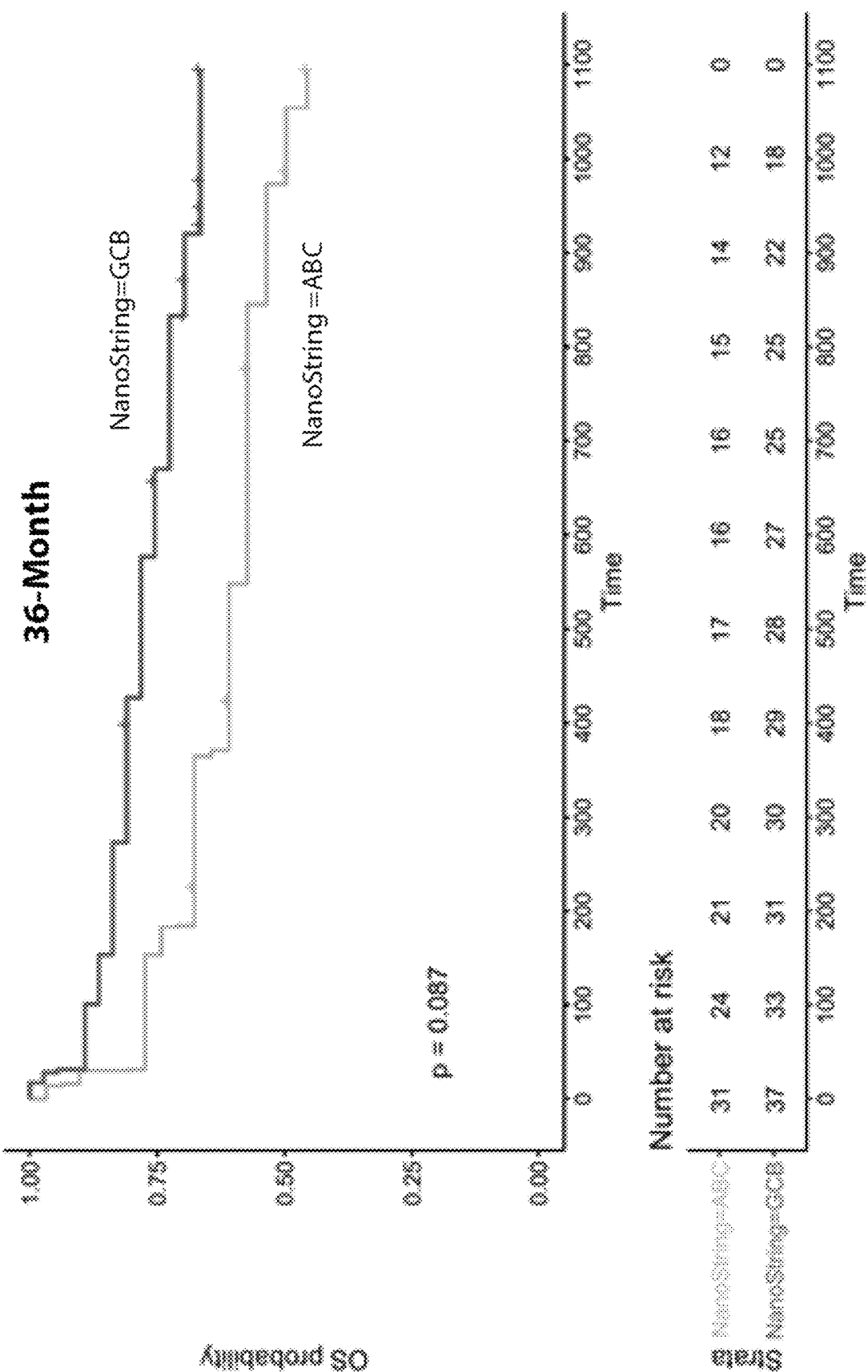
Figure 3E:
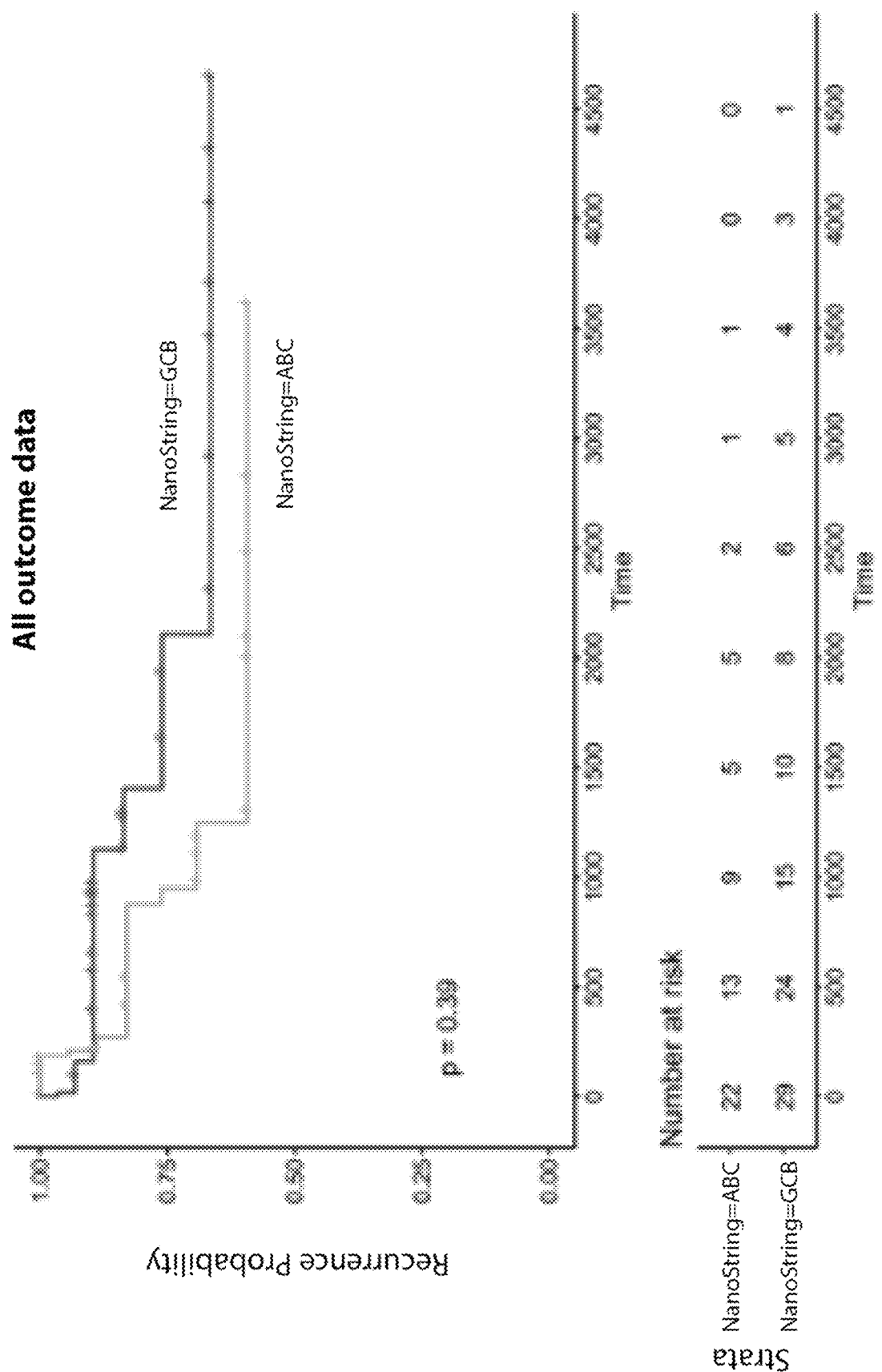
Figure 3F:
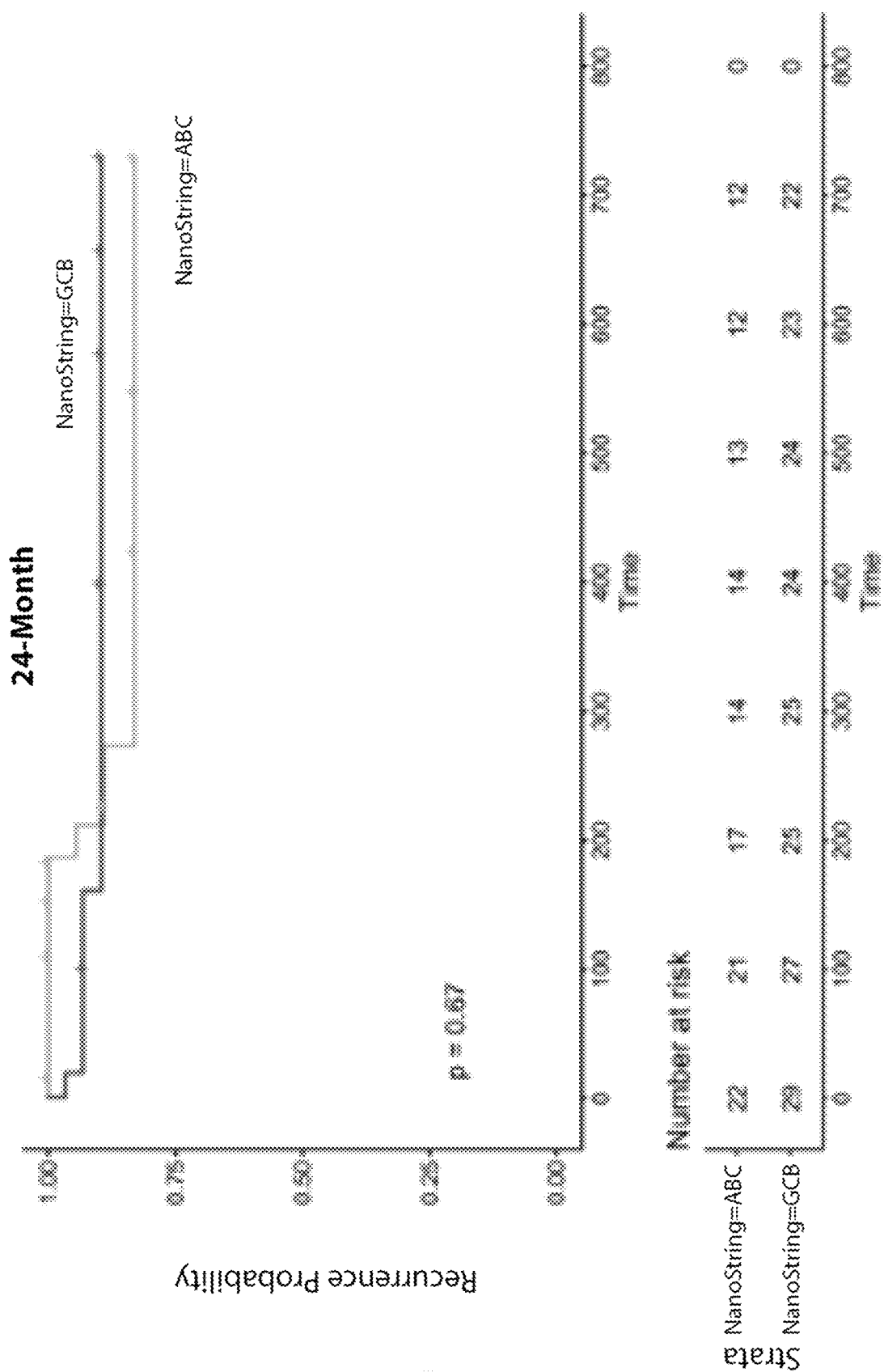
Figure 3G:
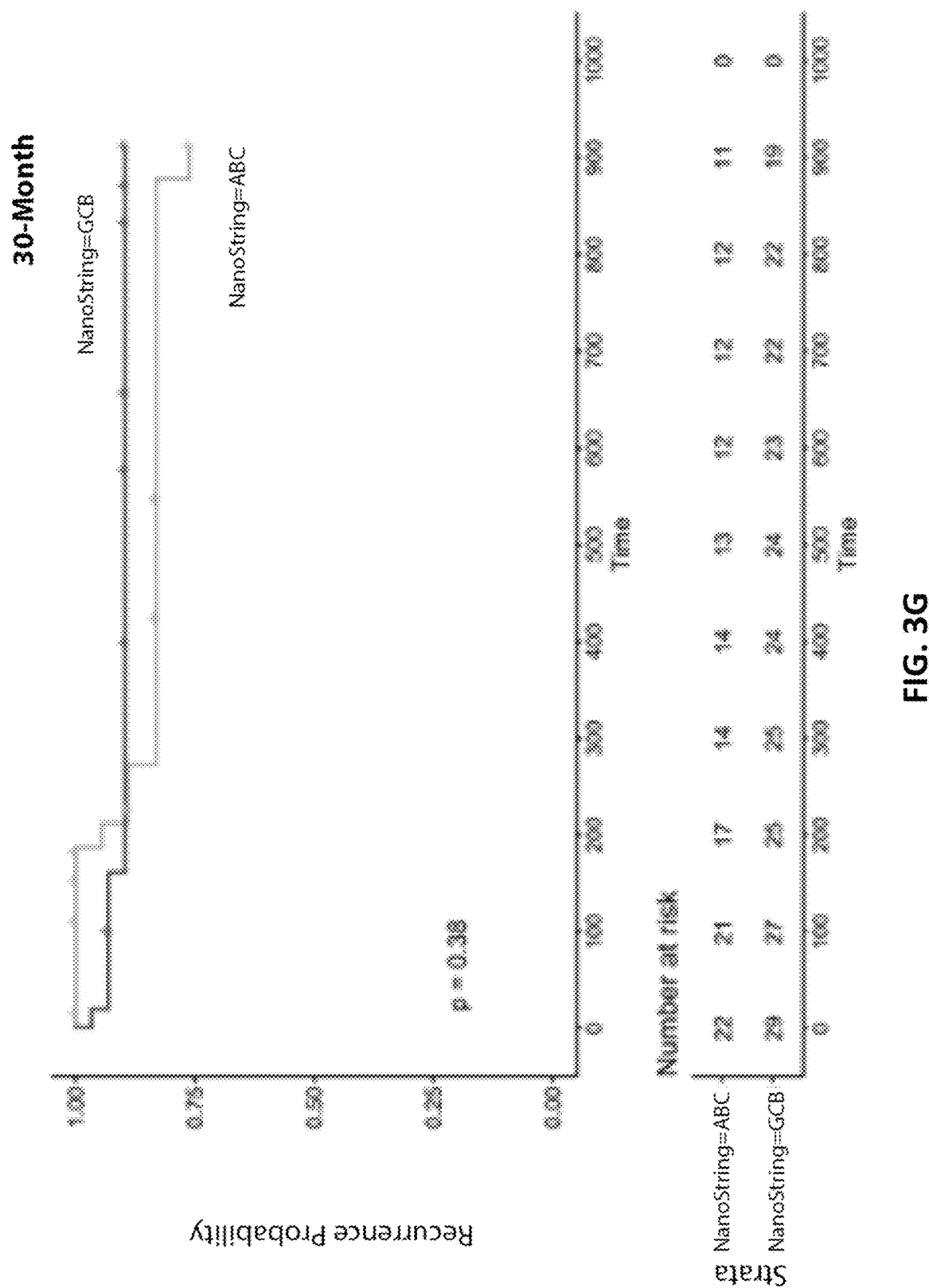
Figure 3H:
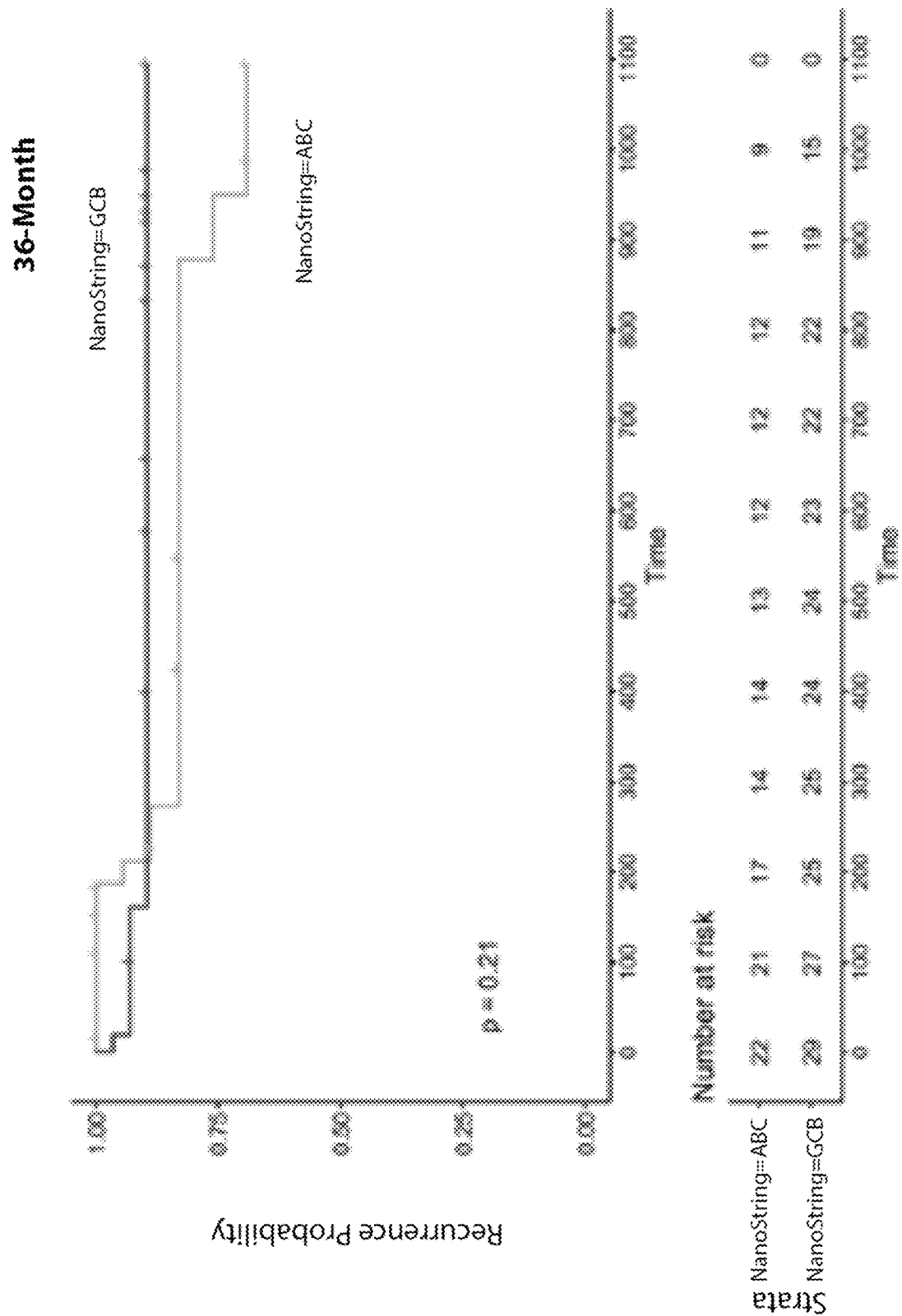

FIGS. 3A-3H illustrate patient outcome analysis according to subtypes in the independent DLBCL cohort determined by the Nanostring's Lymph2Cx assay. FIGS. 3A-3D show overall survival in ABC and GCB as determined by the Nanostring's Lymph2Cx assay at various defining points (FIG. 3A: overall; FIG. 3B: 24-month, FIG. 3C: 30-month; and FIG. 3D: 36-month); and FIGS. 3E-3H show recurrence in ABC and GCB as determined by the Nanostring's Lymph2Cx assay at various defining points (FIG. 3E: overall; FIG. 3F: 24-month, FIG. 3G: 30-month; and FIG. 3H: 36-month). In FIGS. 3A-3H, the survival of GCB subtype is shown in black lines and the survival of ABC subtype is showed in grey lines.

Figure 4A:
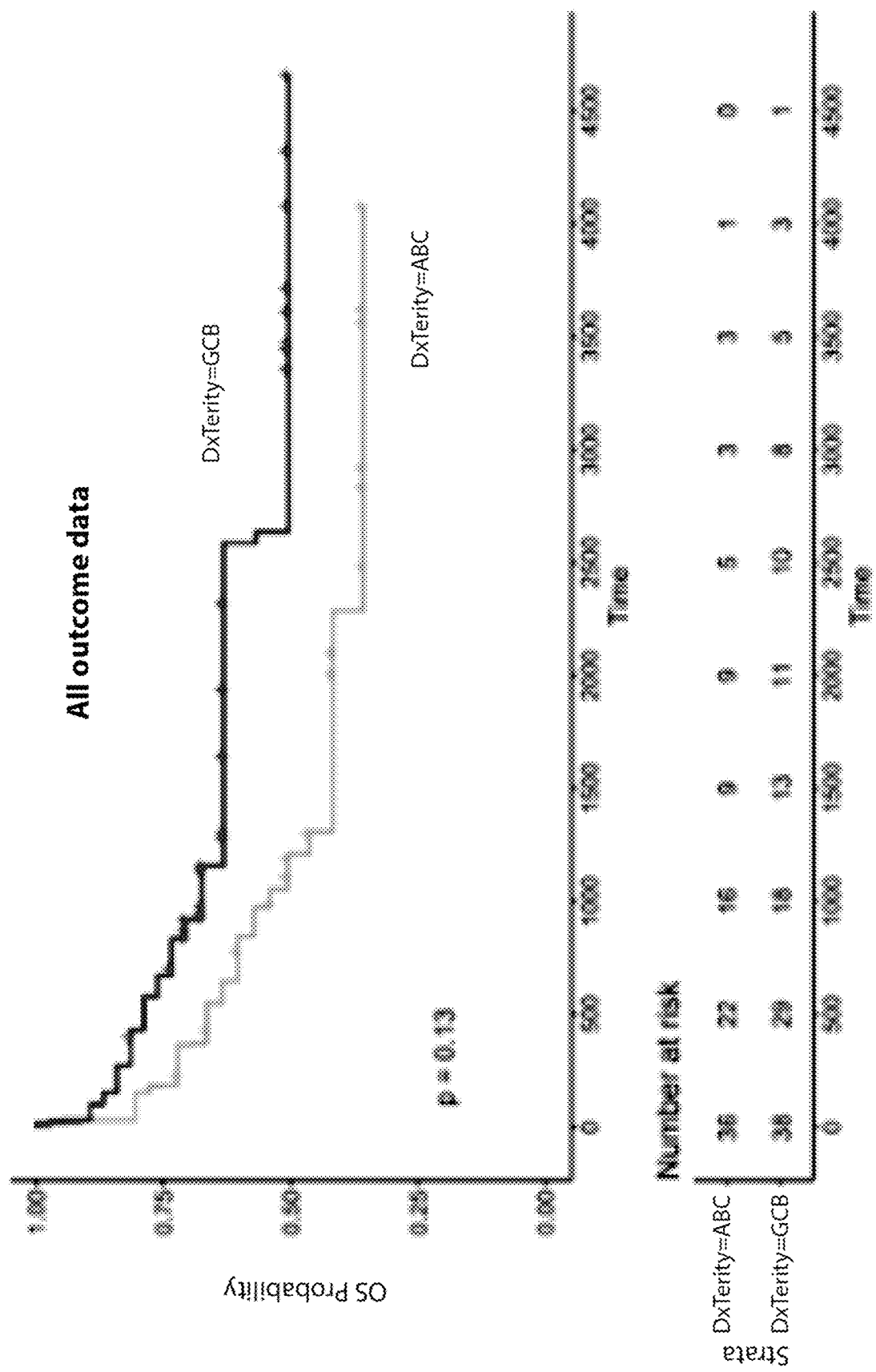
Figure 4B:
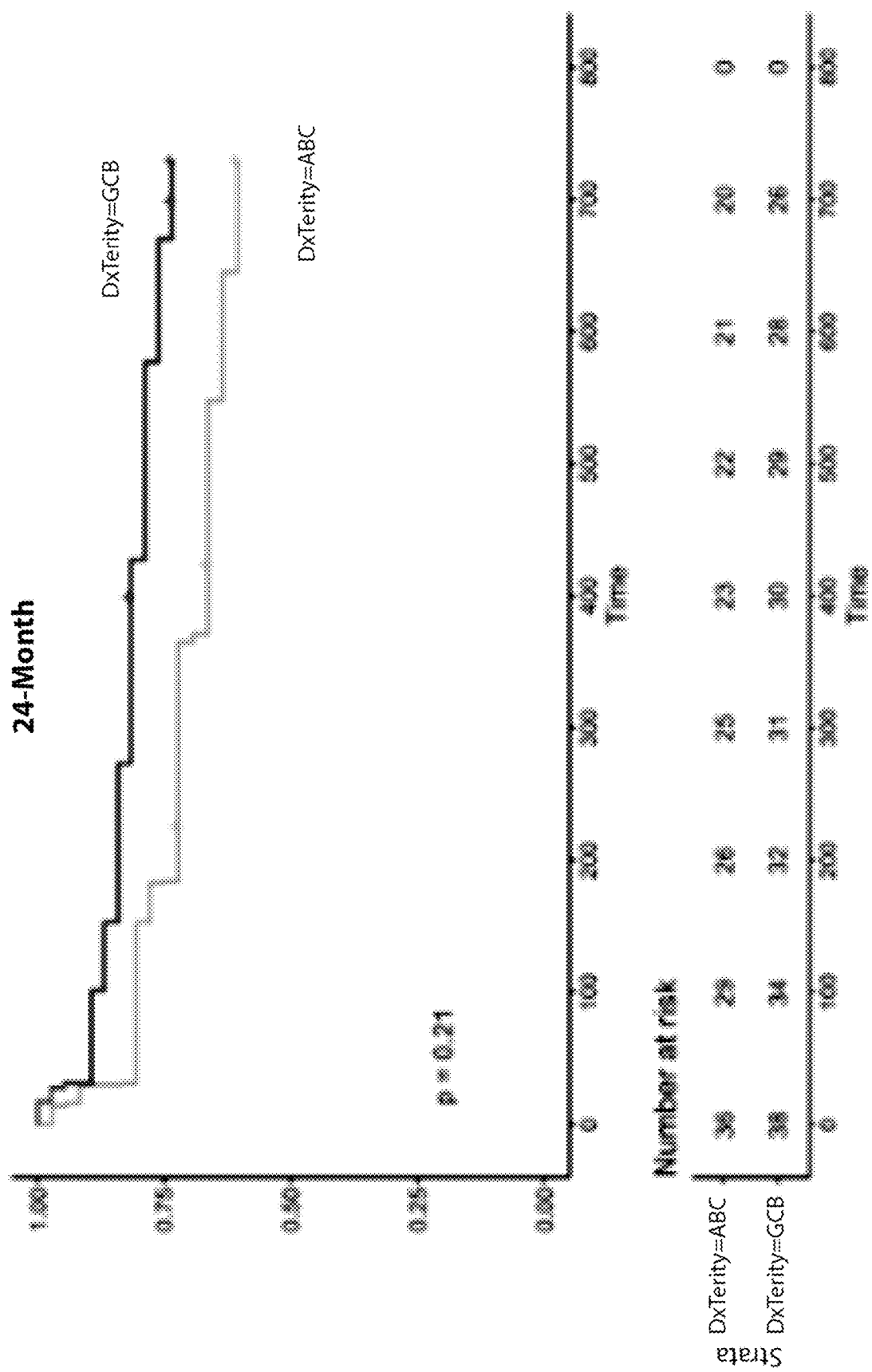
Figure 4C:
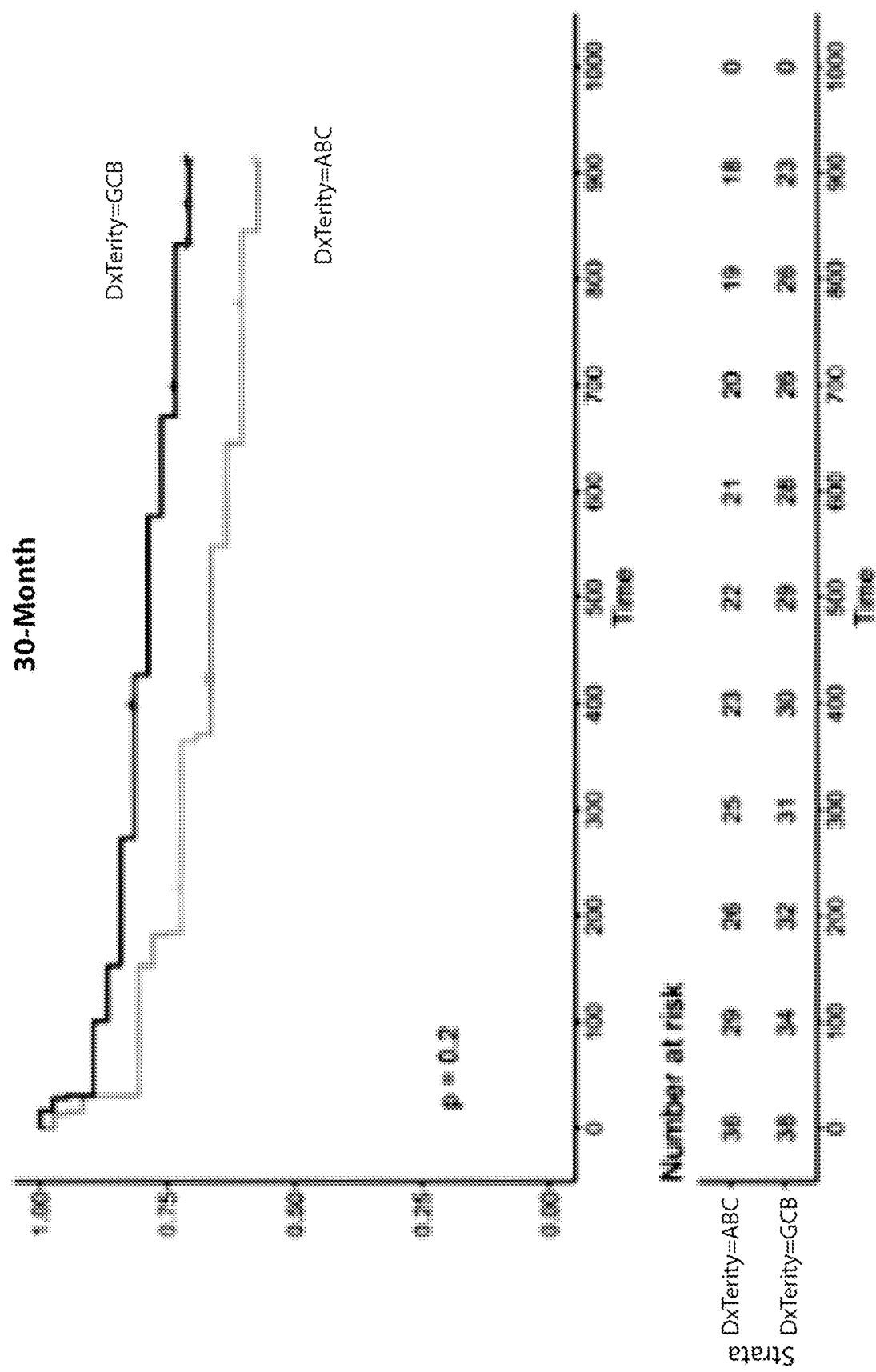
Figure 4D:
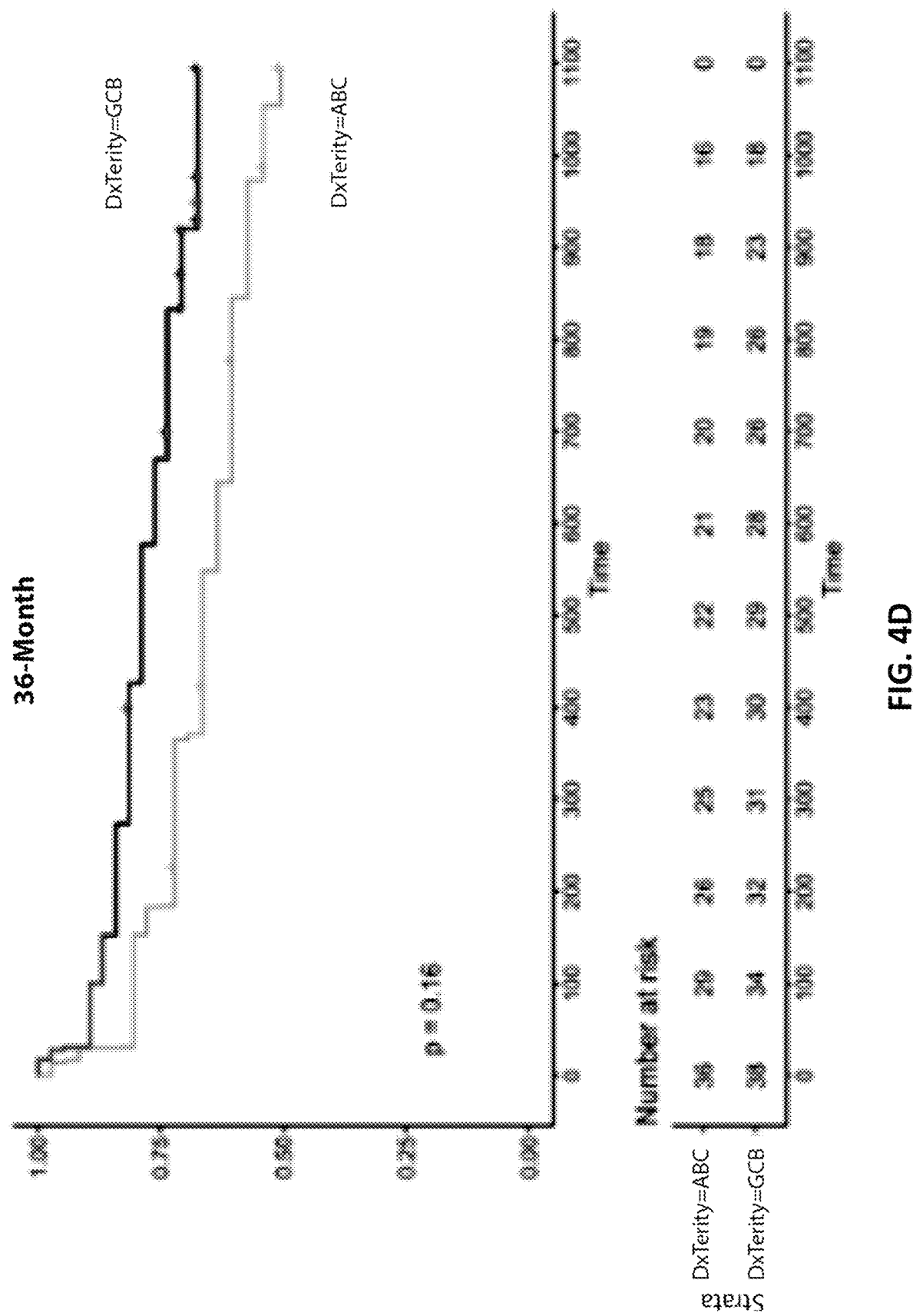
Figure 4E:
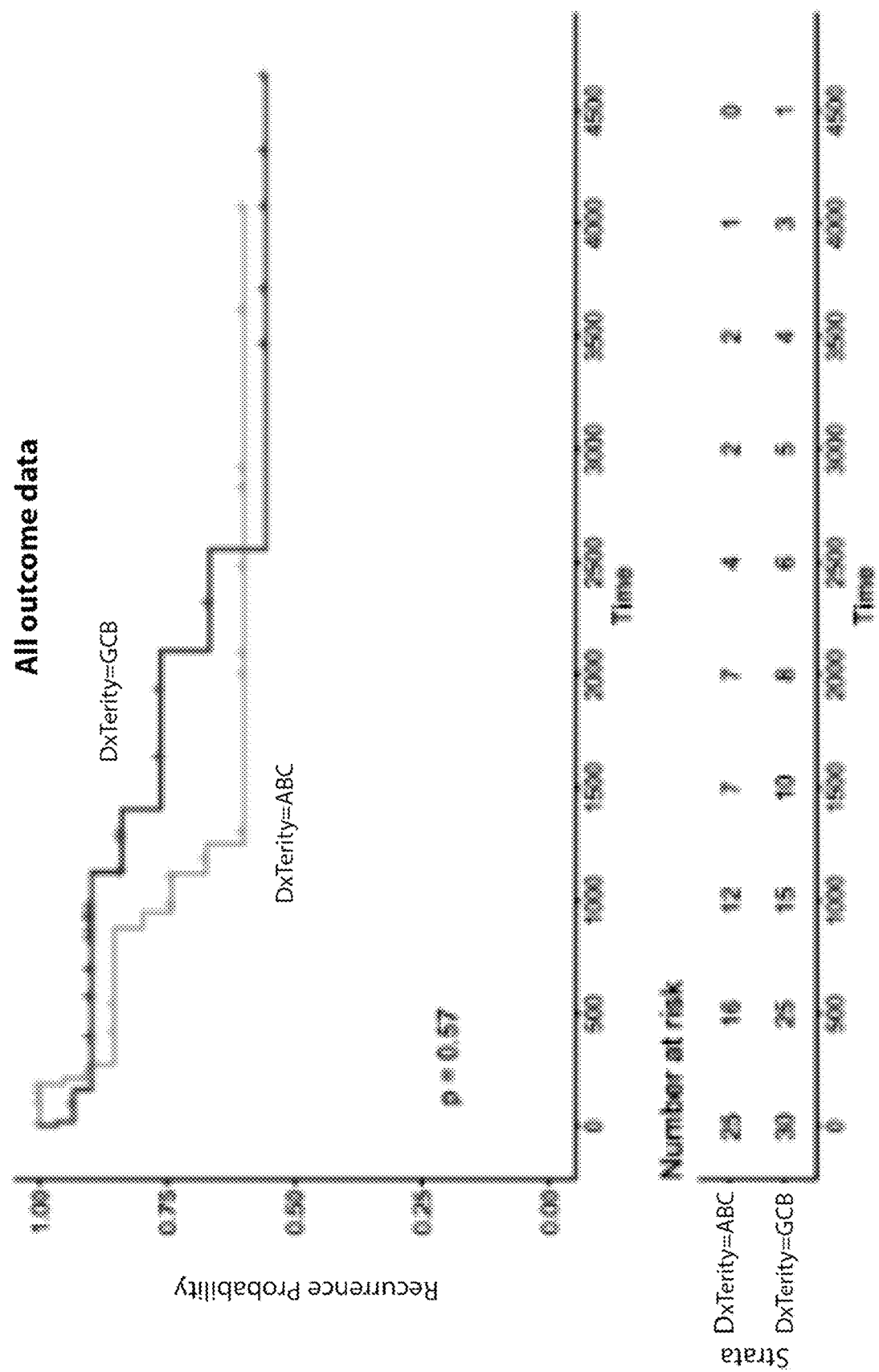
Figure 4F:
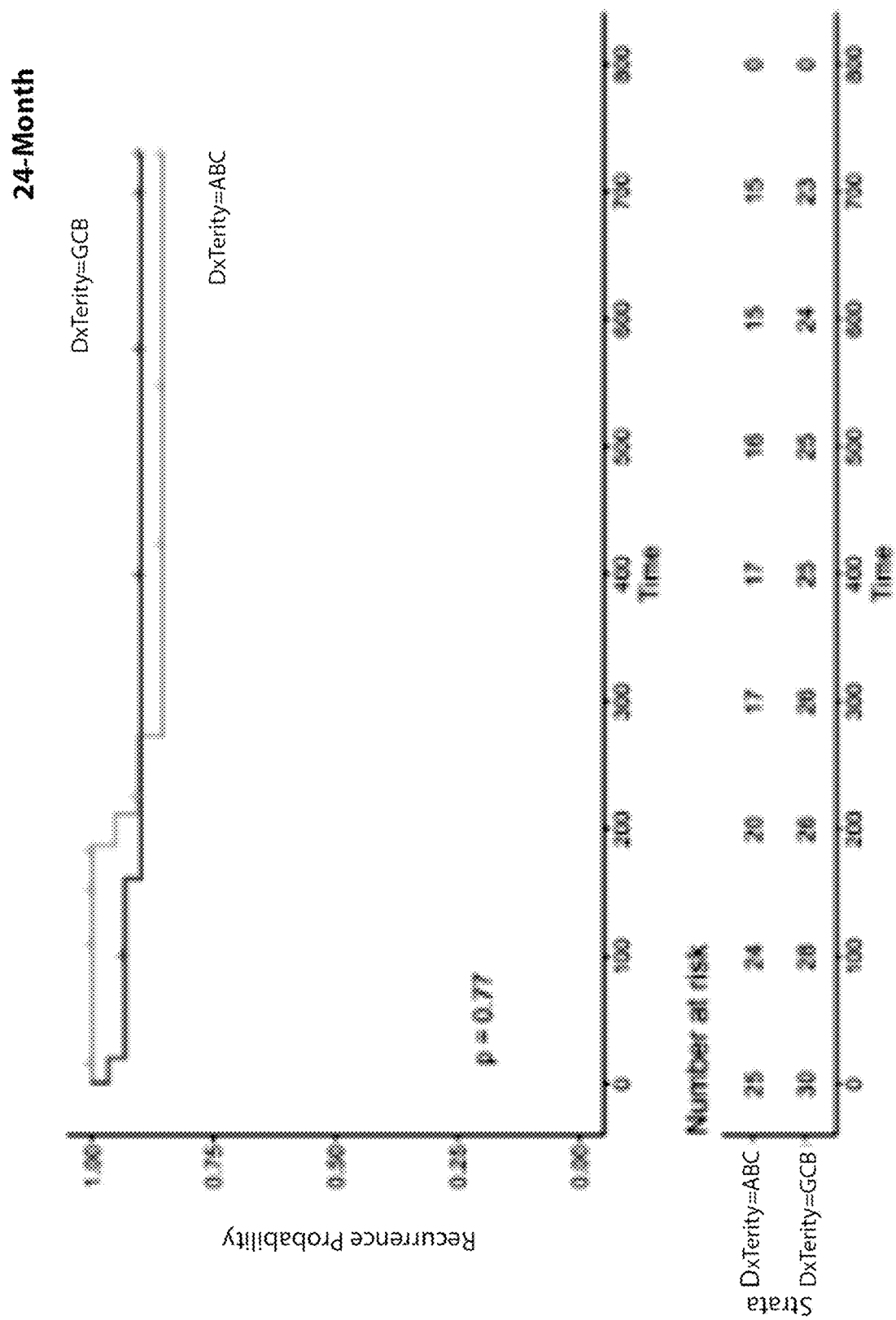
Figure 4G:
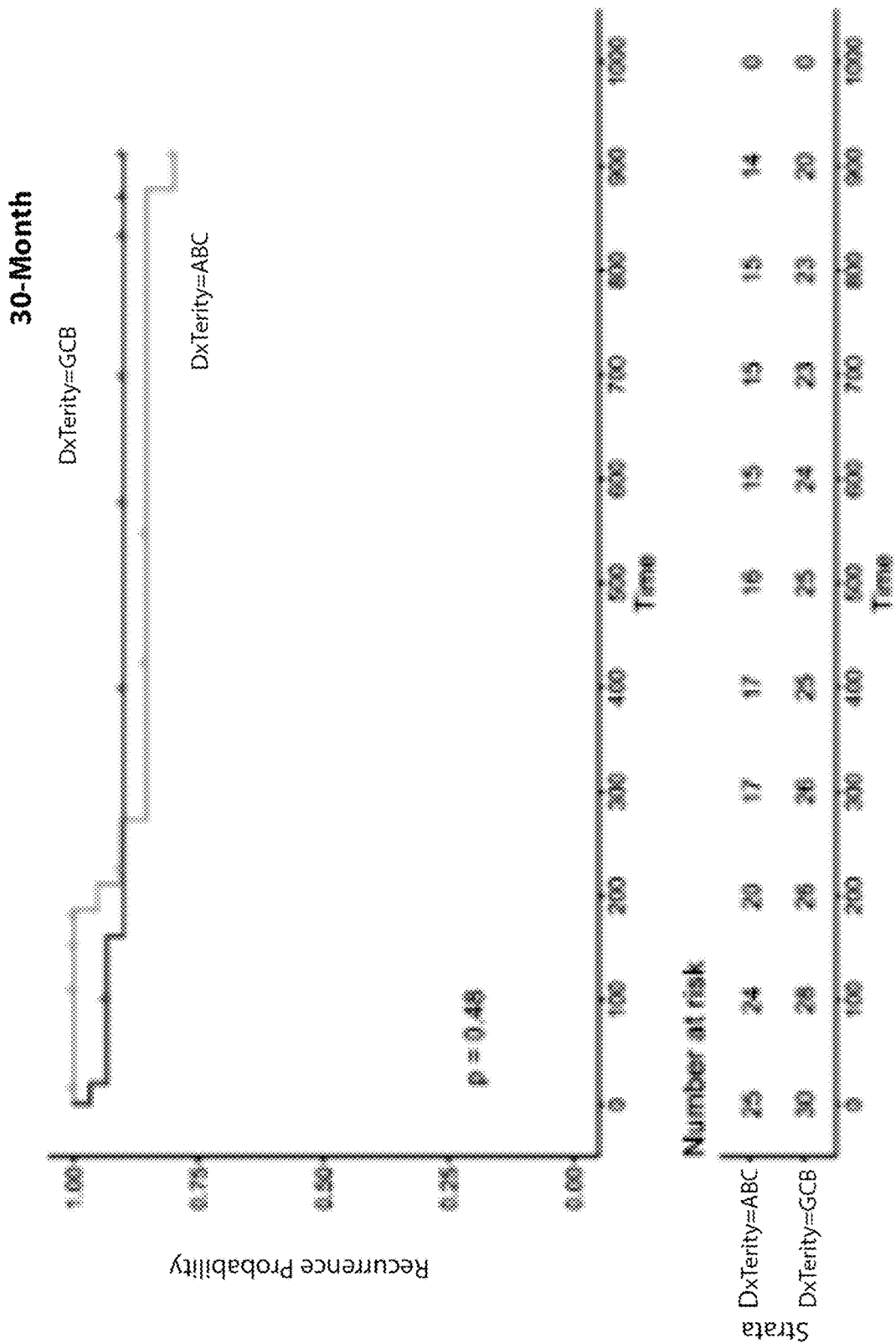
Figure 4H:
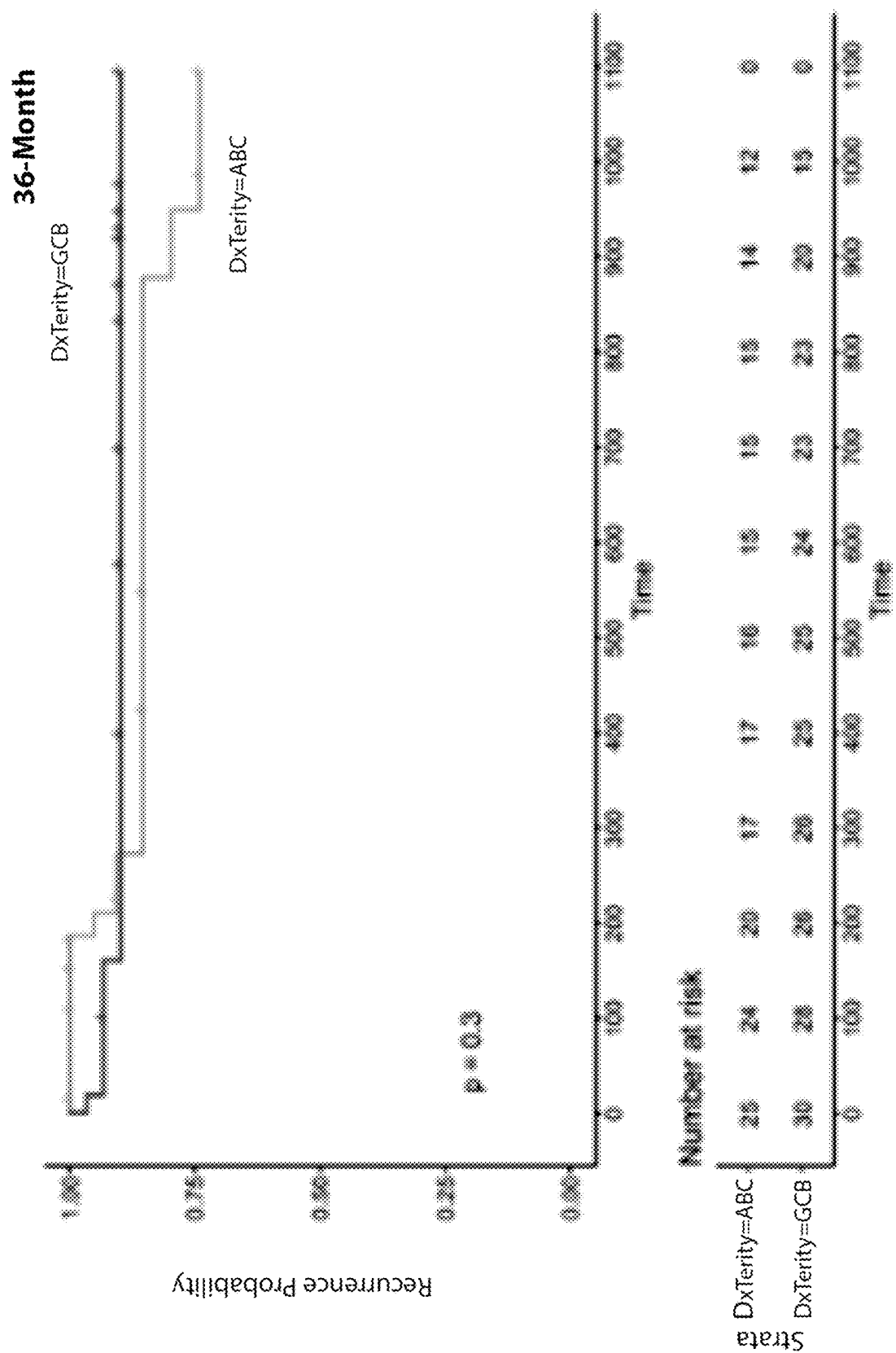

FIGS. 4A-4H illustrate patient outcome analysis according to subtypes in the independent DLBCL cohort determined by the DxTerity DLBCL COO assay. FIGS. 4A-4D show overall survival in ABC and GCB as determined by the DxTerity DLBCL COO assay at various defining points (FIG. 4A: overall; FIG. 4B: 24-month, FIG. 4C: 30-month; and FIG. 4D: 36-month); and FIGS. 4E-4H shows recurrence in ABC and GCB as determined by the DxTerity DLBCL COO assay at various defining points (FIG. 4E: overall; FIG. 4F: 24-month, FIG. 4G: 30-month; and FIG. 4H: 36-month). In FIGS. 4A-4H, the survival of GCB subtype is shown in black lines and the survival of ABC subtype is showed in grey lines.

5. DETAILED DESCRIPTION OF THE INVENTION

Diffuse large B-cell lymphoma (DLBCL) is a heterogeneous group of B-cell lymphomas. Gene expression profiling (GEP) studies have shown that DLBCL can be divided into subtypes of germinal center B-cell-like (GCB), activated B-cell-like (ABC), and unclassified tumors (see Alizadeh et al., Nature 403: 503-511, 2000; Wright G, et al., Proc Natl Acad Sci USA 100:9991-9996, 2003; Scott D W, et al., Blood. 123:1214-1217, 2014) The GCB and ABC subtypes have different pathogenetic mechanisms that may impact the outcomes of DLBCL patients on targeted therapies (Nyman et al., Mod Pathol 22:1094-1101, 2009; Hans, et al., Blood 103:275-282, 2004; Choi et al., Clin Cancer Res 15:5494-5502, 2009; Meyer P N, et al., J Clin Oncol. 29:200-207, 2011; Natkunam Y, et al., J Clin Oncol 26:447-454, 2008)

For example, lenalidomide has a significant single-agent activity in diffuse large B-cell lymphoma (DLBCL). Furthermore, it can be combined with R-CHOP (rituximab plus cyclophosphamide, doxorubicin, vincristine, and prednisone) to form $R^2$CHOP in treating DLBCL, especially ABC tumors. Therefore, the assignment into cell of origin (COO) groups is becoming increasingly important with the emergence of novel therapies that have selective biological activity in GCB or ABC sub-groups.

Despite the robustness of GEP, such as such as Lymph2Cx assay in subclassifying DLBCL, substantial time, cost, technical expertise, and resources are required. Because it is currently impractical to perform GEP analysis on every patient with DLBCL, various IHC algorithms have been developed to predict COO. These algorithms use different combinations of antibodies to DLBCL-related proteins to obtain a desirable result. The results of the algorithms developed by Hans et al and Choi et al have correlated well with the corresponding GEP results and also demonstrated survival differences between the GCB and non-GCB DLBCL groups (see Choi, et al., Clin Cancer Res 15:5494-5502, 2009; and Muris et al., J Pathol 208:714-723, 2006). The IHC assays use standard, formalin-fixed, paraffin-embedded (FFPE) tumor tissues. The Hans' algorithm uses three antibodies: CD10, MUM1, and Bcl-6 to classify DLBCL into GCB and non-GCB (including ABC and unclassified) subtypes (Hans, et al., Blood 103:275-282, 2004). It resulted in a concordance of about 80% when compared with the GEP classification (Hans, et al., Blood 103:275-282, 2004). The Choi algorithm uses GCET1, CD10, Bcl-6, MUM1, and FOXP1 to determined COO of DLBCL and derived a greater than 85% concordance in a single study to the GEP classification (Choi et al., Clin Cancer Res 15:5494-5502, 2009). However, variability from inter-laboratory and inter-observer performance and concern about the robustness of the IHC assays have been reported. Provided herein are methods that address the above-mentioned issues and provide other advantages.

5.1 Definitions

As used herein, and unless otherwise specified, the terms "treat," "treating," and "treatment" refer to an action that occurs while a patient is suffering from the specified cancer, which reduces the severity of the cancer or retards or slows the progression of the cancer.

The term "sensitivity" or "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least about 5%, or more, in the effectiveness of the tumor treatment.

As used herein, the terms "compound" and "treatment compound" are used interchangeably, and include lenalidomide.

As used herein, and unless otherwise specified, the term "therapeutically effective amount" of a compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "responsiveness" or "responsive" when used in reference to a treatment refers to the degree of effectiveness of the treatment in lessening or decreasing the symptoms of a disease, e.g., DLBCL, being treated. For example, the term "increased responsiveness" when used in reference to a treatment of a cell or a subject refers to an increase in the effectiveness in lessening or decreasing the symptoms of the disease compared to a reference treatment (e.g., of the same cell or subject, or of a different cell or subject) when measured using any methods known in the art. In certain embodiments, the increase in the effectiveness is at least about 5%, at least about 10%, at least about 20%, at least about 30%, at least about 40%, or at least about 50%.

As used herein, the terms "effective subject response," "effective patient response," and "effective patient tumor response" refer to any increase in the therapeutic benefit to the patient. An "effective patient tumor response" can be, for example, about 5%, about 10%, about 25%, about 50%, or about 100% decrease in the rate of progress of the tumor. An "effective patient tumor response" can be, for example, about 5%, about 10%, about 25%, about 50%, or about 100% decrease in the physical symptoms of a cancer. An "effective patient tumor response" can also be, for example, about 5%, about 10%, about 25%, about 50%, about 100%, about 200%, or more increase in the response of the patient, as measured by any suitable means, such as gene expression, cell counts, assay results, tumor size, etc.

An improvement in the cancer (e.g., DLBCL or a subtype thereof) or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about 10%, about 20%, about 30%, about 40%, about 50%, about 60%, about 70%, about 80%, or about 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

A "biological marker" or "biomarker" is a substance whose detection indicates a particular biological state, such as, for example, the presence of a type of cancer. In some embodiments, biomarkers can be determined individually. In other embodiments, several biomarkers can be measured simultaneously.

The terms "polypeptide" and "protein," as used interchangeably herein, refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

The term "antibody," "immunoglobulin," or "Ig" as used interchangeably herein, encompasses fully assembled antibodies and antibody fragments that retain the ability to specifically bind to the antigen. Antibodies provided herein include, but are not limited to, synthetic antibodies, monoclonal antibodies, polyclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to CRBN antigen (e.g., one or more complementarity determining regions (CDRs) of an anti-CRBN antibody). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. In some embodiments, the anti-CRBN antibodies are fully human, such as fully human monoclonal CRBN antibodies. In certain embodiments, antibodies provided herein are IgG antibodies, or a subclass thereof (e.g., human IgG1 or IgG4).

The terms "antigen binding domain," "antigen binding region," "antigen binding fragment," and similar terms refer to the portion of an antibody that comprises the amino acid residues that interact with an antigen and confer on the binding agent its specificity and affinity for the antigen (e.g., the CDR). The antigen binding region can be derived from any animal species, such as rodents (e.g., rabbit, rat, or hamster) and humans. In some embodiments, the antigen binding region is of human origin.

The term "epitope" as used herein refers to a localized region on the surface of an antigen that is capable of binding to one or more antigen binding regions of an antibody, that has antigenic or immunogenic activity in an animal, such as a mammal (e.g., a human), and that is capable of eliciting an immune response. An epitope having immunogenic activity is a portion of a polypeptide that elicits an antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic. Epitopes usually consist of chemically active surface groupings of molecules, such as amino acids or sugar side chains, and have specific three dimensional structural characteristics as well as specific charge characteristics. A region of a polypeptide contributing to an epitope may be contiguous amino acids of the polypeptide, or the epitope may come together from two or more non-contiguous regions of the polypeptide. The epitope may or may not be a three-dimensional surface feature of the antigen.

The terms "fully human antibody" and "human antibody" are used interchangeably herein and refer to an antibody that comprises a human variable region and, in some embodiments, a human constant region. In specific embodiments, the terms refer to an antibody that comprises a variable region and a constant region of human origin. The term "fully human antibody" includes antibodies having variable and constant regions corresponding to human germline immunoglobulin sequences as described by Kabat et al., *Sequences of Proteins of Immunological Interest*, U.S. Department of Health and Human Services, NIH Publication No. 91-3242 (5th ed. 1991).

The phrase "recombinant human antibody" includes human antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse or a cow) that is transgenic and/or transchromosomal for human immunoglobulin genes (see, e.g., Taylor et al., *Nucl. Acids Res.* 1992, 20:6287-6295) or antibodies prepared, expressed, created, or isolated by any other means that involves splicing of human immunoglobulin gene sequences to other DNA sequences. Such recombinant human antibodies can have variable and constant regions derived from human germline immunoglobulin sequences. See Kabat et al., *Sequences of Proteins of Immunological Interest*, U.S. Department of Health and Human Services, NIH Publication No. 91-3242 (5th ed. 1991). In certain embodiments, however, such recombinant human antibodies are subjected to in vitro mutagenesis (or, when an animal transgenic for human Ig sequences is used, in vivo somatic mutagenesis) and thus the amino acid sequences of the heavy chain variable and light chain variable regions of the recombinant antibodies are sequences that, while derived from and related to human germline heavy chain variable and light chain variable sequences, may not naturally exist within the human antibody germline repertoire in vivo.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody," as used herein, is an antibody produced by a single hybridoma or other cell, wherein the antibody immunospecifically binds to only an epitope as determined, e.g., by ELISA or other antigen-binding or competitive binding assay known in the art or in the Examples provided herein. The term "monoclonal" is not limited to any particular method for making the antibody. For example, monoclonal antibodies provided herein may be made by the hybridoma method as described in Kohler et al., *Nature* 1975, 256:495-497, or may be isolated from phage libraries using the techniques as described herein. Other methods for the preparation of clonal cell lines and of monoclonal antibodies expressed thereby are well known in the art. See, e.g., *Short Protocols in Molecular Biology*, Chapter 11 (Ausubel et al., eds., John Wiley and Sons, New York, 5th ed. 2002). Other exemplary methods of producing other monoclonal antibodies are provided in the Examples herein.

"Polyclonal antibodies" as used herein refers to an antibody population generated in an immunogenic response to a protein having many epitopes and thus includes a variety of different antibodies directed to the same or to different epitopes within the protein. Methods for producing polyclonal antibodies are known in the art. See, e.g., *Short Protocols in Molecular Biology*, Chapter 11 (Ausubel et al., eds., John Wiley and Sons, New York, 5th ed. 2002).

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute.

The terms "isolated" and "purified" refer to isolation of a substance (such as mRNA, DNA, or protein) such that the substance comprises a substantial portion of the sample in which it resides, i.e., greater than the portion of the substance that is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

As used herein, the term "bound" indicates direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and embodiments where the attachment is indirect.

The term "sample" as used herein relates to a material or mixture of materials, typically, although not necessarily, in fluid form, containing one or more components of interest. In some embodiments, a sample can be a biological sample. "Biological sample" as used herein refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include, but are not limited to, whole blood, partially purified blood, PBMC, tissue biopsies, and the like.

The term "analyte" as used herein refers to a known or unknown component of a sample.

The term "capture agent" as used herein refers to an agent that binds an mRNA or protein through an interaction that is sufficient to permit the agent to bind and to concentrate the mRNA or protein from a heterogeneous mixture.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts (calcium, magnesium, sodium, or potassium salts in particular). Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical co-crystals wherein the crystalline molecular complexes containing a therapeutic compound and one or more additional non-volatile compound(s) (referred to herein as counter-molecule(s)). A counter-molecule in a pharmaceutical co-crystal is typically a non-toxic pharmaceutically acceptable molecule, such as, for example, food additives, preservatives, pharmaceutical excipients, or other active pharmaceutical ingredients (API). In some embodiments, pharmaceutical co-crystals enhance certain physicochemical properties of drug products (e.g., solubility, dissolution rate, bioavailability, and/or stability) without compromising the chemical structural integrity of the API. See, e.g., Jones et al., *MRS Bulletin* 2006, 31, 875-879; Trask, *Mol. Pharmaceutics* 2007, 4(3):301-309; Schultheiss & Newman, *Crystal Growth & Design* 2009, 9(6):2950-2967; Shan & Zaworotko, *Drug Discovery Today* 2008, 13(9/10):440-446; and Vishweshwar et al., *J. Pharm. Sci.* 2006, 95(3):499-516.

As used herein, and unless otherwise specified, the term "stereoisomer" encompasses all enantiomerically/stereomerically pure and enantiomerically/stereomerically enriched compounds of this invention.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff, ed., 5th ed. 1995), and *Design of Prodrugs* (H. Bundgaard, ed., Elsevier, New York 1985).

It should also be noted compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, or nitrogen-15 enriched compounds. In some embodiments, isotopologues provided herein are deuterium enriched compounds. In some embodiments, isotopologues provided herein are deuterium enriched compounds, where the deuteration occurs on the chiral center.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning: A Laboratory Manual* (2d ed. 1989); Glover, ed., *DNA Cloning*, Volumes I and II (1985); Gait, ed., *Oligonucleotide Synthesis* (1984); Hames & Higgins, eds., *Nucleic Acid Hybridization* (1984); Hames & Higgins, eds., *Transcription and Translation* (1984); Freshney, ed., *Animal Cell Culture: Immobilized Cells and Enzymes* (IRL Press, 1986); *Immunochemical Methods in Cell and Molecular Biology* (Academic Press, London); Scopes, *Protein Purification: Principles and Practice* (Springer Verlag, N.Y., 2d ed. 1987); and Weir & Blackwell, eds., *Handbook of Experimental Immunology*, Volumes I-IV (1986).

5.2 Methods of Predicting ABC Subtype of DLBCL and Methods of Treating

In one aspect, provided herein is a method of predicting if a subject has an Activated B Cell-like (ABC) subtype or non-ABC subtype of Diffuse Large B-Cell Lymphoma (DLBCL), comprising: (a) obtaining a sample from the subject; (b) measuring the expression levels of CD10, Bcl-6, MUM1, and FOXP1 in the sample; (c) determining a composite score based on the expression levels of CD10, Bcl-6, MUM1, and FOXP1; and (d) predicting if the subject has an ABC subtype or a non-ABC subtype of DLBCL based on the composite score. In some embodiments, the method comprises predicting if the subject has an ABC subtype of DLBCL based on the composite score. In other embodiments, the method comprises predicting if the subject has a non-ABC subtype of DLBCL based on the composite score.

In some embodiments, the subject is a human subject having DLBCL or suspected of having DLBCL.

In some embodiments, the sample is obtained from a tissue of the subject containing DLBCL cells. More detailed description of the sample (or biological sample) is provided in Section 5.7 below.

The expression levels of CD10, Bcl-6, MUM1, and FOXP1 in the sample can be measured using various methods known in the art and described in Section 5.8 below. In a specific embodiment, the expression levels of CD10, Bcl-6, MUM1, and FOXP1 in the sample are measured by an immunohistochemistry (IHC) method. In some embodiments, the expression levels of one or more of CD10, Bcl-6, MUM1, and FOXP1 are measured together. In other embodiments, the expression level of each of CD10, Bcl-6, MUM1, and FOXP1 is measured in separate experiments. Any antibodies that bind to CD10, Bcl-6, MUM1, and FOXP1 and can produce acceptable results in an IHC method can be used according to the present methods.

Figure 2A:
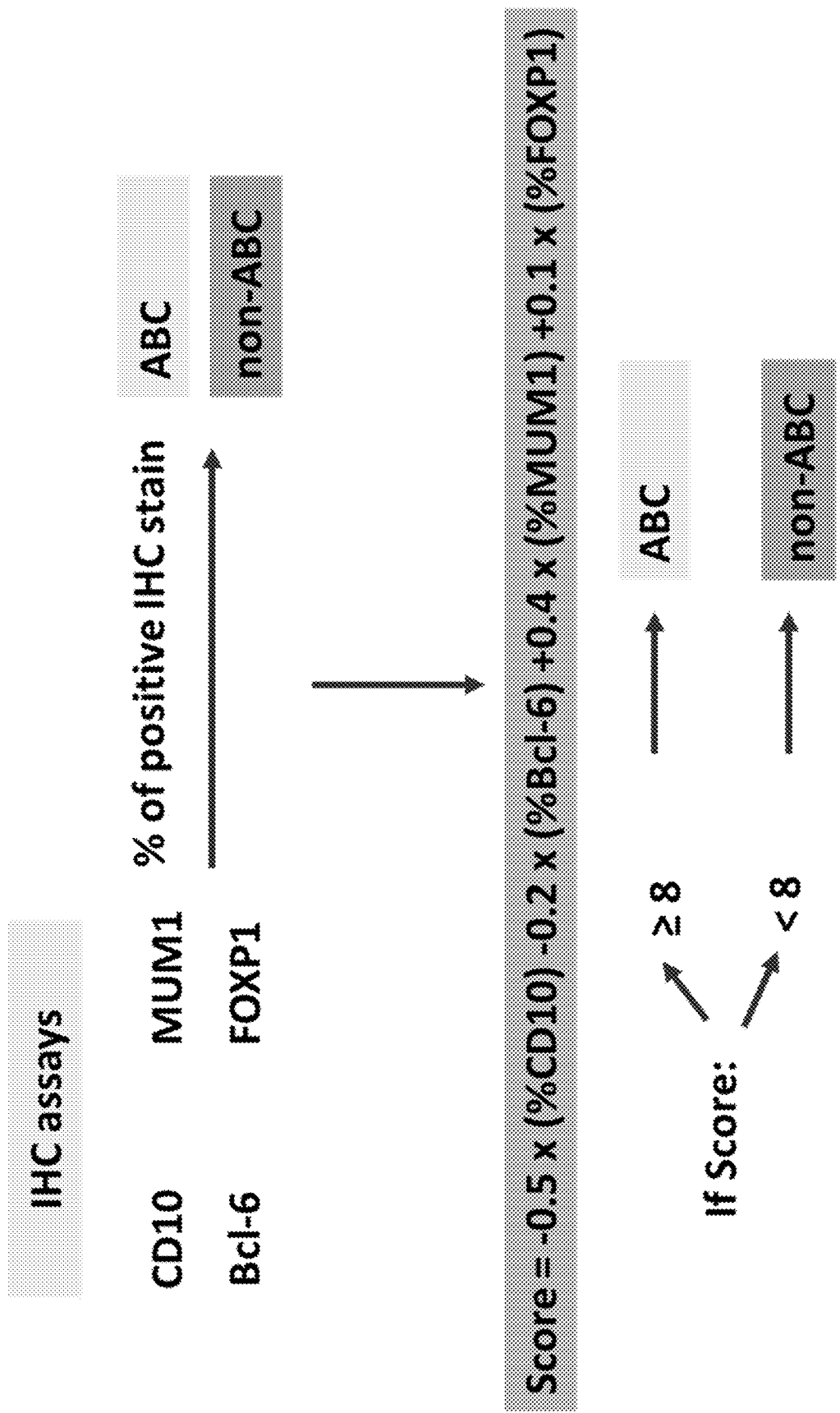
FIG. 2A and FIG. 2B depict the IHC algorithms for subtype classification of DLBCL.

In some embodiments, the method provided herein is based on the percentages of the cells that are positively stained by antibodies that bind to CD10, Bcl-6, MUM1, and FOXP1 in an IHC assay. Thus, in some embodiments, the method provided herein further comprises determining (i) a first percentage, the first percentage being the percentage of the positively stained cells determined by the IHC method using an anti-CD10 antibody, (ii) a second percentage, the second percentage being the percentage of the positively stained cells determined by the IHC method using an anti-Bcl-6 antibody, (iii) a third percentage, the third percentage being the percentage of the positively stained cells determined by the IHC method using an anti-MUM1 antibody, and (iv) a fourth percentage, the fourth percentage being the percentage of the positively stained cells determined by the IHC method using an anti-FOXP1 antibody. Then, a composite score is calculated based on the following formula: composite score=−0.5×the first percentage−0.2×the second percentage+0.4×the third percentage+0.1×the fourth percentage. In some embodiments, the method comprises predicting that the subject has the ABC subtype of DLBCL if the composite score is 8 or higher than 8. In some embodiments, the method comprises predicting that the subject does not the ABC subtype of DLBCL if the composite score is less than 8. The method is illustrated in FIG. 2A.

Figure 2B:
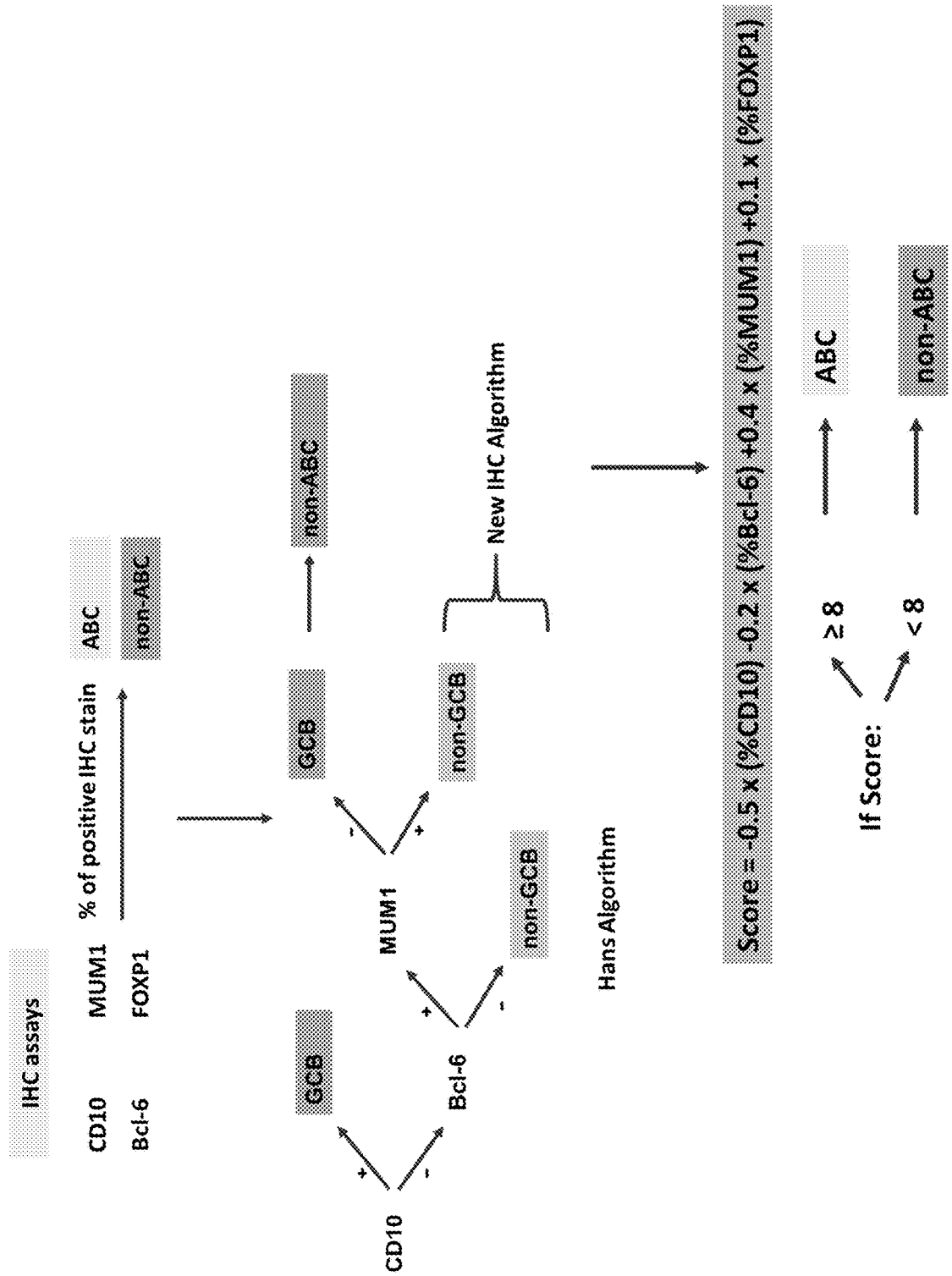

In some embodiments, the method is used in combination with another method for predicting the subtype of DLBCL. For example, FIG. 2B illustrate such a combination method. The method applies the Hans algorithm first and then applies the above-mentioned algorithm only to the non-GCB samples of the Hans result in order to call out ABC samples (FIG. 2B).

In another aspect, provided herein is a method of treating a subject predicted to have an ABC subtype of DLBCL. In some embodiments, the method comprises (i) predicting if the subject has an ABC subtype of DLBCL using a method comprising: (a) obtaining a sample from the subject; (b) measuring the expression levels of CD10, Bcl-6, MUM1, and FOXP1; (c) determining a composite score based on the expression levels of CD10, Bcl-6, MUM1, and FOXP1; and (d) predicting if the subject has an ABC subtype of DLBCL based on the composite score, and (ii) administering to the subject predicted to have the ABC subtype of DLBCL a therapeutically effective amount of a treatment compound. In a specific embodiment, the treatment compound is lenalidomide or a stereoisomer or a mixture of stereoisomers, tautomer, pharmaceutically acceptable salt, solvate, isotopologue, prodrug, hydrate, co-crystal, clathrate, or a polymorph thereof.

In another aspect, provided herein is a method of treating a subject predicted to have a non-ABC subtype of DLBCL. In some embodiments, the method comprises (i) predicting if the subject has a non-ABC subtype of DLBCL using a method comprising: (a) obtaining a sample from the subject; (b) measuring the expression levels of CD10, Bcl-6, MUM1, and FOXP1; (c) determining a composite score based on the expression levels of CD10, Bcl-6, MUM1, and FOXP1; and (d) predicting if the subject has a non-ABC subtype of DLBCL based on the composite score, and (ii) administering to the subject predicted to have the non-ABC subtype of DLBCL a therapeutically effective amount of a treatment compound suitable for treating the non-ABC subtype of DLBCL.

In some embodiments, the subject is a human subject having DLBCL or suspected of having DLBCL. In some embodiments, the sample is obtained from a tissue of the subject containing DLBCL cells. More detailed description of the sample (or biological sample) is provided in Section 5.7 below.

The expression levels of CD10, Bcl-6, MUM1, and FOXP1 in the sample can be measured using various methods known in the art and described in Section 5.8 below. In a specific embodiment, the expression levels of CD10, Bcl-6, MUM1, and FOXP1 in the sample are measured by an immunohistochemistry (IHC) method. In some embodiments, the expression levels of one or more of CD10, Bcl-6, MUM1, and FOXP1 are measured together. In other embodiments, the expression level of each of CD10, Bcl-6, MUM1, and FOXP1 is measured in separate experiments. Any antibodies that bind to CD10, Bcl-6, MUM1, and FOXP1 and can produce acceptable results in an IHC method can be used according to the present methods.

In some embodiments, the method provided herein is based on the percentages of the cells that are positively stained by antibodies that bind to CD10, Bcl-6, MUM1, and FOXP1 in an IHC assay. Thus, in some embodiments, the method provided herein further comprises determining (i) a first percentage, the first percentage being the percentage of the positively stained cells determined by the IHC method using an anti-CD10 antibody, (ii) a second percentage, the second percentage being the percentage of the positively stained cells determined by the IHC method using an anti-Bcl-6 antibody, (iii) a third percentage, the third percentage being the percentage of the positively stained cells determined by the IHC method using an anti-MUM1 antibody, and (iv) a fourth percentage, the fourth percentage being the percentage of the positively stained cells determined by the IHC method using an anti-FOXP1 antibody. Then, a composite score is calculated based on the following formula: composite score=−0.5×the first percentage−0.2×the second percentage+0.4×the third percentage+0.1×the fourth percentage. In some embodiments, the method comprises predicting that the subject has the ABC subtype of DLBCL if the composite score is 8 or higher than 8. In some embodiments, the method comprises predicting that the subject does not the ABC subtype of DLBCL if the composite score is less than 8.

In some embodiments, the method is used in combination with another method for predicting the subtype of DLBCL. The treatment compounds and administration methods are described in more detail in the sections below.

In another aspect, provided herein is a method of predicting if a subject has an Activated B Cell-like (ABC) subtype or non-ABC subtype of Diffuse Large B-Cell Lymphoma (DLBCL), comprising: (a) obtaining a sample from the subject; (b) measuring the expression levels of CD10, MUM1, and FOXP1 in the sample; (c) determining a composite score based on the expression levels of CD10, MUM1, and FOXP1; and (d) predicting if the subject has an ABC subtype or a non-ABC subtype of DLBCL based on the composite score. In some embodiments, the method comprises predicting if the subject has an ABC subtype of DLBCL based on the composite score. In other embodiments, the method comprises predicting if the subject has a non-ABC subtype of DLBCL based on the composite score.

In some embodiments, the subject is a human subject having DLBCL or suspected of having DLBCL.

In some embodiments, the sample is obtained from a tissue of the subject containing DLBCL cells. More detailed description of the sample (or biological sample) is provided in Section 5.7 below.

The expression levels of CD10, MUM1, and FOXP1 in the sample can be measured using various methods known in the art and described in Section 5.8 below. In a specific embodiment, the expression levels of CD10, MUM1, and FOXP1 in the sample are measured by an immunohistochemistry (IHC) method. In some embodiments, the expression levels of one or more of CD10, MUM1, and FOXP1 are measured together. In other embodiments, the expression level of each of CD10, MUM1, and FOXP1 is measured in separate experiments. Any antibodies that bind to CD10, MUM1, and FOXP1 and can produce acceptable results in an IHC method can be used according to the present methods.

In some embodiments, the method provided herein is based on the percentages of the cells that are positively stained by antibodies that bind to CD10, MUM1, and FOXP1 in an IHC assay. Thus, in some embodiments, the method provided herein further comprises determining (i) a first percentage, the first percentage being the percentage of the positively stained cells determined by the IHC method using an anti-CD10 antibody, (ii) a second percentage, the second percentage being the percentage of the positively stained cells determined by the IHC method using an anti-MUM1 antibody, and (iii) a third percentage, the third percentage being the percentage of the positively stained cells determined by the IHC method using an anti-FOXP1 antibody. Then, a composite score is calculated based on the following formula: composite score=−1.4367173−0.0238081×the first percentage+0.01051371×the second percentage+0.02111138×the third percentage. In some embodiments, the method comprises predicting that the subject has the ABC subtype of DLBCL if the composite score is 0 or higher than 0. In some embodiments, the method comprises predicting that the subject does not the ABC subtype of DLBCL if the composite score is less than 0.

In some embodiments, the method is used in combination with another method for predicting the subtype of DLBCL. For example, in some embodiments, the method applies the Hans algorithm first and then applies the above-mentioned algorithm only to the non-GCB samples of the Hans result in order to call out ABC samples.

In another aspect, provided herein is a method of treating a subject predicted to have an ABC subtype of DLBCL. In some embodiments, the method comprises (i) predicting if the subject has an ABC subtype of DLBCL using a method comprising: (a) obtaining a sample from the subject; (b) measuring the expression levels of CD10, MUM1, and FOXP1; (c) determining a composite score based on the expression levels of CD10, MUM1, and FOXP1; and (d) predicting if the subject has an ABC subtype of DLBCL based on the composite score, and (ii) administering to the subject predicted to have the ABC subtype of DLBCL a therapeutically effective amount of a treatment compound. In a specific embodiment, the treatment compound is lenalidomide or a stereoisomer or a mixture of stereoisomers, tautomer, pharmaceutically acceptable salt, solvate, isotopologue, prodrug, hydrate, co-crystal, clathrate, or a polymorph thereof.

In another aspect, provided herein is a method of treating a subject predicted to have a non-ABC subtype of DLBCL. In some embodiments, the method comprises (i) predicting if the subject has a non-ABC subtype of DLBCL using a method comprising: (a) obtaining a sample from the subject; (b) measuring the expression levels of CD10, MUM1, and FOXP1; (c) determining a composite score based on the expression levels of CD10, MUM1, and FOXP1; and (d) predicting if the subject has a non-ABC subtype of DLBCL based on the composite score, and (ii) administering to the subject predicted to have the non-ABC subtype of DLBCL a therapeutically effective amount of a treatment compound suitable for treating the non-ABC subtype of DLBCL.

In some embodiments, the subject is a human subject having DLBCL or suspected of having DLBCL. In some embodiments, the sample is obtained from a tissue of the subject containing DLBCL cells. More detailed description of the sample (or biological sample) is provided in Section 5.7 below.

The expression levels of CD10, MUM1, and FOXP1 in the sample can be measured using various methods known in the art and described in Section 5.8 below. In a specific embodiment, the expression levels of CD10, MUM1, and FOXP1 in the sample are measured by an immunohistochemistry (IHC) method. In some embodiments, the expression levels of one or more of CD10, MUM1, and FOXP1 are measured together. In other embodiments, the expression level of each of CD10, MUM1, and FOXP1 is measured in separate experiments. Any antibodies that bind to CD10, MUM1, and FOXP1 and can produce acceptable results in an IHC method can be used according to the present methods.

In some embodiments, the method provided herein is based on the percentages of the cells that are positively stained by antibodies that bind to CD10, MUM1, and FOXP1 in an IHC assay. Thus, in some embodiments, the method provided herein further comprises determining (i) a first percentage, the first percentage being the percentage of the positively stained cells determined by the IHC method using an anti-CD10 antibody, (ii) a second percentage, the second percentage being the percentage of the positively stained cells determined by the IHC method using an anti-MUM1 antibody, and (iii) a third percentage, the third percentage being the percentage of the positively stained cells determined by the IHC method using an anti-FOXP1 antibody. Then, a composite score is calculated based on the following formula: composite score=−1.4367173−0.0238081×the first percentage+0.01051371×the second percentage+0.02111138×the third percentage. In some embodiments, the method comprises predicting that the subject has the ABC subtype of DLBCL if the composite score is 0 or higher than 0. In some embodiments, the method comprises predicting that the subject does not the ABC subtype of DLBCL if the composite score is less than 0.

In some embodiments, the method is used in combination with another method for predicting the subtype of DLBCL. The treatment compounds and administration methods are described in more detail in the sections below.

5.3 Treatment Compounds

In some embodiments, the methods provided herein comprise administering a treatment compound (or compound) to the subject predicted to have the ABC subtype of DLBCL.

In some embodiments, the treatment compound is more effective and/or safer for treating ABC subtype of DLBCL than other subtypes of DLBCL. In some embodiments, the compound administered to a DLBCL (e.g., ABC subtype of DLBCL) patient is 3-(4-amino-1-oxo-1,3-dihydro-isoindol-2-yl)-piperidine-2,6-dione (lenalidomide; REVLIMID®), or a stereoisomer thereof; or a pharmaceutically acceptable salt, solvate, hydrate, co-crystal, clathrate thereof; or a polymorph thereof. Such compounds can be formulated for the appropriate route of administration using techniques known in the art. Lenalidomide can be prepared using the following exemplary method.

Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100 W bulb situated 2 cm away was shining on the flask. The mixture was filtered and the solid was washed with methylene chloride (50 mL). The filtrate was washed with water (2×100 mL), brine (100 mL) and dried. The solvent was removed in vacuo and the residue was purified by flash chromatography (hexane/ethyl acetate, 8/2) to afford 19 g (96%) of the product as a yellow solid: mp 70.0-71.5° C.; 1H NMR (CDCl$_3$) δ 8.12-8.09 (dd, J=1.3 and 7.8 Hz, 1H), 7.97-7.94 (dd, J=1.3 and 8.2 Hz, 1H), 7.54 (t, J=8.0 Hz, 1H). 5.15 (s, 2H), 4.00 (s, 3H); $^{13}$C NMR (CDCl$_3$) δ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 CH$_3$CN/0.1% H$_3$PO$_4$(aq) 7.27 min(98.92%); Anal. Calcd for C$_9$H$_8$NO$_4$Br: C, 39.44; H, 2.94; N, 5.11; Br, 29.15. Found: C, 39.46; H, 3.00; N, 5.00; Br, 29.11.

t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL) and dried. The solvent was removed in vacuo and the residue was purified by flash chromatography (3% CH$_3$OH in methylene chloride) to afford 2.84 g (60%) of crude product which was used directly in the next reaction: 1H NMR (CDCl$_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H). 1.46 (s, 9H); HPLC, Waters Nova-Pak C18, 3.9×150 mm, 4 micron, 1 mL/min, 240 nm, 25/75 CH$_3$CN/0.1% H$_3$PO$_4$(aq) 6.75 min(99.94%).

N-(1-oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL) for 1 hour. The mixture was then stirred at room temperature for another hour. Ether (40 mL) was added and the resulting mixture was stirred for 30 minutes. The slurry was filtered, washed with ether and dried to afford 3.3 g of the product: 1H NMR (DMSO-d$_6$) δ 8.45 (d, J=8.1 Hz, 1H), 8.15 (d, J=7.5 Hz, 1H), 7.83 (t, J=7.9 Hz. 1H), 7.24 (s, 1H), 6.76 (s, 1H), 4.93 (s, 2H), 4.84-4.78 (dd, J=4.8 and 10.4 Hz, 1H), 2.34-2.10 (m, 4H); $^{13}$C NMR (DMSO-d$_6$) δ 173.03, 171.88, 165.96, 143.35, 137.49, 134.77, 130.10, 129.61, 126.95, 53.65, 48.13, 31.50, 24.69; Anal. Calcd for C$_{13}$H$_{13}$N$_3$O$_6$: C, 50.82; H, 4.26; N, 13.68. Found: C, 50.53; H. 4.37; N, 13.22.

(S)-3-(1-oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g. 11.3 mmol). After 30 min, triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL) and dried. The solvent was removed in vacuo and the solid residue was slurried with ethyl acetate (20 mL) to give 2.2 g (75%) of the product as a white solid: mp 285° C.; 1H NMR (DMSO-d$_6$) δ: 1.04 (s, 1H), 8.49-8.45 (dd, J=0.8 and 8.2 Hz, 1H), 8.21-8.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}$C NMR (DMSO-d$_6$) δ 172.79, 170.69, 165.93, 143.33, 137.40, 134.68, 130.15, 129.60, 127.02, 51.82, 48.43, 31.16. 22.23; HPLC, Waters Nove-Pak/C18, 3.9×150 mm, 4 micron, 1 mL/min, 240 nm, 20/80 CH$_3$CN/ 0.1% H$_3$PO$_4$(aq) 3.67 min(100%); Anal. Calcd for C$_{13}$H$_n$N$_3$O$_5$: C, 53.98; H, 3.83; N, 14.53. Found: C, 53.92; H, 3.70; N, 14.10.

3-(4-amino-1-oxo-1,3-dihydro-isoindol-2-yl)-piperidine-2,6-dione

A mixture of (S)-3-(1-oxo-4-nitroisoindolin-2-yl)piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered and dried to afford 0.46 g (51%) of the product as a white solid: mp 235.5-239° C.; $^1$H NMR (DMSO-d$_6$) δ 11.01 (s, 1H). 7.19 (t, J=7.6 Hz, 1H). 6.90 (d. J=7.3 Hz, 1H), 6.78 (d, J=7.8 Hz, 1H), 5.42 (s, 2H). 5.12 (dd. J=5.1 and 13.1 Hz, 1H), 4.17 (dd, J=17.0 and 28.8 Hz, 2H), 2.92-2.85 (m, 1H). 2.64-2.49 (m, 1H). 2.34-2.27 (m, 1H), 2.06-1.99 (m, 1H); $^{13}$C NMR (DMSO-d$_6$) δ 172.85, 171.19, 168.84, 143.58, 132.22. 128.79, 125.56, 116.37, 110.39, 51.48, 45.49, 31.20, 22.74; HPLC. Waters Nova-Pak/C18, 3.9×150 mm, 4 micron, 1 mL/min, 240 nm, 10/90 CH$_3$CN/0.1% H$_3$PO$_4$(aq) 0.96 min(100%); Chiral analysis, Daicel Chiral Pak AD, 40/60 Hexane/IPA, 6.60 min(99.42%); Anal. Calcd for C$_{13}$H$_{13}$N$_3$O$_3$: C, 60.23; H, 5.05; N, 16.21. Found: C, 59.96; H. 4.98; N, 15.84.

Lenalidomide (3-(4-Amino-1-oxo-1,3-dihydro-isoindol-2-yl)-piperidine-2,6-dione) may also be prepared by methods known in the art, for example, as provided in *Drugs of the Future*, 2003, 28(5): 425-431, the entirety of which is incorporated by reference.

5.4 Administration Methods

In some embodiments of the various methods provided herein, a treatment compound (e.g., lenalidomide) is administered to a patient predicted to have the ABC subtype of DLBCL. Also provided herein are methods of treating patients who have been previously treated for cancer (e.g., DLBCL or a subtype thereof) but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer (e.g., DLBCL or a subtype thereof).

In certain embodiments, a therapeutically or prophylactically effective amount of the treatment compound (e.g., lenalidomie) is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiments, the therapeutically or prophylactically effective amount is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a treatment compound for the conditions described herein lie within the range of from about 0.1 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 mg to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg per day. In a specific embodiment, the treatment compound is lenalidomie, or a stereoisomer or a mixture of stereoisomers, tautomer, pharmaceutically acceptable salt, solvate, isotopologue, prodrug, hydrate, co-crystal, clathrate, or a polymorph thereof.

In a specific embodiment, the recommended starting dosage may be 0.5, 1, 2, 3, 4, 5, 10, 15, 20, 25, or 50 mg per day. In another embodiment, the recommended starting dosage may be 0.5, 1, 2, 3, 4, or 5 mg per day. The dose may be escalated to 10, 15, 20, 25, 30, 35, 40, 45, or 50 mg per day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, fda.gov/cder/cancer/animalframe.htm). For example, a dose of 1 mg/kg/day for a 65 kg human is approximately equal to 38 mg/m$^2$/day.

In certain embodiments, the amount of the compound (e.g., lenalidomide) administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound (e.g., lenalidomie) administered is sufficient to provide a plasma concentration of the compound at steady state, ranging from about 5 to about 100 nM, about 5 to about 50 nM, about 10 to about 100 nM, about 10 to about 50 nM, or from about 50 to about 100 nM.

As used herein, the term "plasma concentration at steady state" is the concentration reached after a period of administration of a compound provided herein, e.g., lenalidomie, or a stereoisomer or a mixture of stereoisomers, tautomer, pharmaceutically acceptable salt, solvate, isotopologue, prodrug, hydrate, co-crystal, clathrate, or a polymorph thereof. Once steady state is reached, there are minor peaks and troughs on the time-dependent curve of the plasma concentration of the compound.

In certain embodiments, the amount of the compound (e.g., lenalidomide) administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound (e.g., lenalidomie) administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound (e.g., lenalidomide) administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of the treatment compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof). In certain embodiments, the patient to be treated with one of the methods provided herein has been treated with anticancer therapy prior to the administration of the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof). In certain embodiments, the patient to be treated with one of the methods provided herein has developed drug resistance to the anticancer therapy.

Depending on the subtype of DLBCL to be treated and the subject's condition, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) may be administered by parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) may be formulated, alone or together, in suitable dosage unit with pharmaceutically acceptable excipients, carriers, adjuvants, and vehicles, appropriate for each route of administration.

In one embodiment, the compound (e.g., lenalidomie, or a stereoisomer or a mixture of stereoisomers, tautomer, pharmaceutically acceptable salt, solvate, isotopologue, prodrug, hydrate, co-crystal, clathrate, or a polymorph thereof) is administered parenterally. In another embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered intravenously.

The compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) can be delivered as a single dose (e.g., a single bolus injection), or over time (e.g., continuous infusion over time or divided bolus doses over time). The compound can be administered repeatedly if necessary, for example, until the patient experiences stable disease or regression, or until the patient experiences disease progression or unacceptable toxicity. For example, stable disease for solid cancers generally means that the perpendicular diameter of measurable lesions has not increased by 25% or more from the last measurement. Therasse et al., *J. Natl. Cancer Inst.* 2000, 92(3):205-216.

Stable disease or lack thereof is determined by methods known in the art such as evaluation of patient symptoms, physical examination, and visualization of the tumor that has been imaged using X-ray, CAT, PET, Mill scan, or other commonly accepted evaluation modalities.

The compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) can be administered once daily (QD) or divided into multiple daily doses such as twice daily (BID), three times daily (TID), and four times daily (QID). In addition, the administration can be continuous (i.e., daily for consecutive days or every day) or intermittent, e.g., in cycles (i.e., including days, weeks, or months of rest without drug). As used herein, the term "daily" is intended to mean that a therapeutic compound, such as lenalidomide, or a stereoisomer or a mixture of stereoisomers, tautomer, pharmaceutically acceptable salt, solvate, isotopologue, prodrug, hydrate, co-crystal, clathrate, or a polymorph thereof, is administered once or more than once each day, for example, for a period of time. The term "continuous" is intended to mean that a therapeutic compound, such as lenalidomide, or a stereoisomer or a mixture of stereoisomers, tautomer, pharmaceutically acceptable salt, solvate, isotopologue, prodrug, hydrate, co-crystal, clathrate, or a polymorph thereof, is administered daily for an uninterrupted period of at least 10 days to 52 weeks. The term "intermittent" or "intermittently" as used herein is intended to mean stopping and starting at either regular or irregular intervals. For example, intermittent administration of the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as lenalidomide, or a stereoisomer or a mixture of stereoisomers, tautomer, pharmaceutically acceptable salt, solvate, isotopologue, prodrug, hydrate, co-crystal, clathrate, or a polymorph thereof, is administered daily or continuously but with a rest period. In certain embodiments, the rest period is the same length as the treatment period. In other embodiments, the rest period has different length from the treatment period. In some embodiments, the length of cycling is 1, 2, 3, 4, 5, 6, 7, 8, 9, or 10 weeks. In some embodiments of cycling, a therapeutic compound, such as lenalidomide, or a stereoisomer or a mixture of stereoisomers, tautomer, pharmaceutically acceptable salt, solvate, isotopologue, prodrug, hydrate, co-crystal, clathrate, or a polymorph thereof, is administered daily for a period of 1, 2, 3, 4, 5, 6, 7, 8, 9, 10, 15, 20, 25, or 30 days, followed by a rest period. In a particular embodiment, the therapeutic compound is administered daily for a period of 5 days of a 4-week cycle. In another particular embodiment, the therapeutic compound is administered daily for a period of 10 days of a 4-week cycle.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered once a day. In another embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered twice a day. In yet another embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered three times a day. In still another embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered four times a day.

In certain embodiments, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered once per day from one day to six months, from one week to three months, from one week to four weeks, from one week to three weeks, or from one week to two weeks. In certain embodiments, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered once per day for one week, two weeks, three weeks, or four weeks. In one embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered once per day for one week. In another embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered once per day for two weeks. In yet another embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered once per day for three weeks. In still another embodiment, the compound (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) is administered once per day for four weeks.

5.5 Combination Therapy

One or more additional therapies, such as additional active ingredients or agents, that can be used in combination with the administration of a compound described herein to treat a DLBCL patient (e.g., a patient having the ABC subtype of DLBCL). In a specific embodiment, one or more additional active ingredients or agents can be used in the methods provided herein with lenalidomide. The one or more additional therapies can be administered prior to, concurrently with, or subsequent to the administration of the compound (e.g., lenalidomide) described herein. Administration of a compound described herein and an additional active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the condition of DLBCL being treated. Routes of administration for the additional active agents or ingredients are known to those of ordinary skill in the art. See, e.g., Physicians' Desk Reference.

In certain embodiments, the compound described herein (e.g., lenalidomide) and an additional active agent are cyclically administered to a patient with DLBCL (e.g., ABC subtype of DLBCL). Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

The additional active agents administered in combination with the compound described herein (e.g., lenalidomide) can be large molecules (e.g., proteins) or small molecules (e.g., synthetic inorganic, organometallic, or organic molecules). In certain embodiments, the additional active agent is an immunomodulatory therapy. In other embodiments, the additional active agent is not a compound described herein. Examples of large molecule active agents include, but are not limited to, hematopoietic growth factors, cytokines, and monoclonal and polyclonal antibodies. In certain embodiments, large molecule active agents are biological molecules, such as naturally occurring or artificially made proteins. Proteins that are useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the disclosure include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPGEN® (Amgen, Thousand Oaks, Calif.).

Inhibitors of ActRII receptors or activin-ActRII inhibitors may be used in the methods and compositions provided herein. ActRII receptors include ActRIIA inhibitors and ActRIIB inhibitors. Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker. Examples of such non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety.

Recombinant and mutated forms of GM-CSF can be prepared as described in U.S. Pat. Nos. 5,391,485; 5,393,870; and 5,229,496; the disclosure of each of which is incorporated herein by reference in its entirety. Recombinant and mutated forms of G-CSF can be prepared as described in U.S. Pat. Nos. 4,810,643; 4,999,291; 5,528,823; and 5,580,755; the disclosure of each of which is incorporated herein by reference in its entirety.

This disclosure encompasses the use of native, naturally occurring, and recombinant proteins. The disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be used in combination with the compound described herein include monoclonal and polyclonal antibodies. Examples of antibodies include, but are not limited to, trastuzumab (HERCEPTIN), rituximab (RITUXAN®), bevacizumab (AVASTIN®), pertuzumab (OMNITARG™), tositumomab (BEXXAR®), edrecolomab (PANOREX®), panitumumab and G250. An immunomodulatory therapy provided herein can also be combined with or used in combination with anti-TNF-alpha antibodies.

In some embodiments, the additional active agent is an immune checkpoint inhibitor. As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217, 149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitors is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In some embodiments, the amount of the checkpoint inhibitor can be determined by standard clinical techniques. A dosage of the checkpoint inhibitor results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, such as at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention and/or treatment of a cancer. It is to be understood that the precise dose of the checkpoint inhibitor to be employed will also depend on the route of administration, and the seriousness of a cancer in a subject, and should be decided according to the judgment of the practitioner and each patient's circumstances.

Large molecule active agents may be administered in the form of anti-cancer vaccines. For example, vaccines that secrete, or cause the secretion of, cytokines such as IL-2, SCF, CXC14 (platelet factor 4), G-CSF, and GM-CSF can be used in the methods, pharmaceutical compositions, and kits of the disclosure. See, e.g., Emens, L. A., et al., Curr. Opinion Mol. Ther. 3(1):77-84 (2001).

Additional active agents that are small molecules can also be used to alleviate adverse effects associated with the administration of a compound described herein. However, like some large molecules, many are believed to be capable of providing a synergistic effect when administered with (e.g., before, after or simultaneously) the immunomodulatory therapy. Examples of small molecule additional active agents include, but are not limited to, anti-cancer agents, antibiotics, immunosuppressive agents, and steroids.

Examples of anti-cancer agents include, but are not limited to: abraxane; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porflmer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®.), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); O$_6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds;

platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific additional active agents include, but are not limited to, oblimersen (GENASENSE®), remicade, docetaxel, celecoxib, melphalan, dexamethasone (DECADRON®), steroids, gemcitabine, cisplatinum, temozolomide, etoposide, cyclophosphamide, temodar, carboplatin, procarbazine, gliadel, tamoxifen, topotecan, methotrexate, ARISA®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate (EMCYT), sulindac, and etoposide.

5.6 Pharmaceutical Compositions

In certain embodiments, the compound provides herein (e.g., lenalidomide) and/or the additional active agent provided herein are formulated in a pharmaceutical composition, and the method provide herein comprises administering a DLBCL patient (e.g., a patient having the ABC subtype of DLBCL) a pharmaceutical composition comprising the compound provided herein (e.g., lenalidomide).

In some embodiments, the pharmaceutical compositions provided herein contain therapeutically effective amounts of one or more of the compounds provided herein and a pharmaceutically acceptable carrier, diluents, or excipient. In some embodiments, the compounds may be formulated as the sole pharmaceutically active ingredient in the composition or may be combined with other active ingredients.

The compounds can be formulated into suitable pharmaceutical compositions for different routes of administration, such as injection, sublingual and buccal, rectal, vaginal, ocular, otic, nasal, inhalation, nebulization, cutaneous, or transdermal. Typically, the compounds described above are formulated into pharmaceutical compositions using techniques and procedures well known in the art (see, e.g., Ansel, *Introduction to Pharmaceutical Dosage Forms*, (7th ed. 1999)).

In the compositions, effective concentrations of one or more compounds or pharmaceutically acceptable salts are mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of DLBCL (e.g., ABC subtype of DLBCL).

The active compound is in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans. The concentration of active compound in the pharmaceutical composition will depend on absorption, tissue distribution, inactivation, and excretion rates of the active compound, the physicochemical characteristics of the compound, the dosage schedule, and amount administered as well as other factors known to those of skill in the art.

The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carriers, vehicles, or diluents. Examples of unit dose forms include ampoules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules, or bottles of pints or gallons. Hence, multiple dose form is a multiple of unit doses which are not segregated in packaging.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solutions or suspensions used for parenteral, intradermal, subcutaneous, or topical application can include any of the following components: a sterile diluents (such as water, saline solution, fixed oil, polyethylene glycol, glycerine, propylene glycol, dimethyl acetamide, or other synthetic solvent), antimicrobial agents (such as benzyl alcohol and methyl parabens), antioxidants (such as ascorbic acid and sodium bisulfate), chelating agents (such as ethylenediaminetetraacetic acid (EDTA)), buffers (such as acetates, citrates, and phosphates), and agents for the adjustment of tonicity (such as sodium chloride or dextrose). Parenteral preparations can be enclosed in ampoules, pens, disposable syringes, or single or multiple dose vials made of glass, plastic, or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolving the compound in aqueous sodium hydroxide, sodium bicarbonate, or hydrochloric acid.

Sustained-release preparations can also be prepared. Suitable examples of sustained-release preparations include semipermeable matrices of solid hydrophobic polymers containing the compound provided herein, which matrices are in the form of shaped articles, e.g., films or microcapsule. Examples of sustained-release matrices include iontophoresis patches, polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular di-sulfate bond formation through thio-disulfide interchange, stabilization may be achieved by modifying sulfhydryl residues, lyophilizing from acidic solutions, controlling moisture content, using appropriate additives, and developing specific polymer matrix compositions.

Lactose-free compositions provided herein can contain excipients that are well known in the art and are listed, for example, in *The U.S. Pharmacopeia (USP)*. In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch, and magnesium stearate.

Further encompassed are anhydrous pharmaceutical compositions and dosage forms containing a compound provided herein. Anhydrous pharmaceutical compositions and dosage forms provided herein can be prepared using anhydrous or low moisture containing ingredients and low moisture or low humidity conditions, as known by those skilled in the art. An anhydrous pharmaceutical composition should be prepared and stored such that its anhydrous nature is maintained. Accordingly, anhydrous compositions are packaged using materials known to prevent exposure to water such that they can be included in suitable formulatory kits. Examples of suitable packaging include, but are not limited to, hermetically sealed foils, plastics, unit dose containers (e.g., vials), blister packs, and strip packs.

Dosage forms or compositions containing active ingredient in the range of 0.001% to 100% with the balance made up from non-toxic carrier may be prepared. In some embodiments, the contemplated compositions contain from about 0.005% to about 95% active ingredient. In other embodiments, the contemplated compositions contain from about 0.01% to about 90% active ingredient. In certain embodiments, the contemplated compositions contain from about 0.1% to about 85% active ingredient. In other embodiments, the contemplated compositions contain from about 0.1% to about 75-95% active ingredient.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to herein above, such as solid cancer or blood born cancer. It is to be understood that such combination therapy constitutes a further aspect of the compositions and methods of treatment provided herein.

Parenteral administration of the compositions includes intravenous, subcutaneous, and intramuscular administrations. Compositions for parenteral administration include sterile solutions ready for injection, sterile dry soluble products, such as lyophilized powders, ready to be combined with a solvent just prior to use, sterile suspensions ready for injection, and sterile emulsions. The solutions may be either aqueous or nonaqueous. The unit dose parenteral preparations are packaged in an ampoule, a vial or a syringe with a needle. All preparations for parenteral administration must be sterile, as is known and practiced in the art.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents, and other pharmaceutically acceptable substances.

Examples of aqueous vehicles include sodium chloride injection, Ringer's injection, isotonic dextrose injection, sterile water injection, dextrose and lactated Ringer's injection. Nonaqueous parenteral vehicles include fixed oils of vegetable origin, such as cottonseed oil, corn oil, sesame oil, and peanut oil. Antimicrobial agents in bacteriostatic or fungistatic concentrations must be added to parenteral preparations packaged in multiple dose containers, which include phenols or cresols, mercurials, benzyl alcohol, chlorobutanol, methyl and propyl-p-hydroxybenzoic acid esters, thimerosal, benzalkonium chloride, and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles, and sodium hydroxide, hydrochloric acid, citric acid, or lactic acid for pH adjustment.

Injectables are designed for local and systemic administration. Typically, a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

Of interest herein are also lyophilized powders, which can be reconstituted for administration as solutions, emulsions, and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, or other suitable agent. The solvent may also contain a buffer, such as citrate, phosphate, or other buffers known to those of skill in the art. Subsequent sterile filtration of the solution followed by lyophilization under standard conditions known to those of skill in the art provides the desired formulation. Generally, the resulting solution will be apportioned into vials for lyophilization. Each vial will contain a single dosage or multiple dosages of the compound. The lyophilized powder can be stored under appropriate conditions, such as at about 4° C. to room temperature.

In one aspect, the lyophilized formulations are suitable for reconstitution with a suitable diluent to the appropriate concentration prior to administration. In one embodiment, the lyophilized formulation is stable at room temperature. In one embodiment, the lyophilized formulation is stable at room temperature for up to about 24 months. In one embodiment, the lyophilized formulation is stable at room temperature for up to about 24 months, up to about 18 months, up to about 12 months, up to about 6 months, up to about 3 months or up to about 1 month. In one embodiment, the lyophilized formulation is stable upon storage under accelerated condition of 40° C./75% RH for up to about 12 months, up to about 6 months or up to about 3 months.

In some embodiments, the lyophilized formulation is suitable for reconstitution with an aqueous solution for intravenous administrations. In certain embodiments, the lyophilized formulation provided herein is suitable for reconstitution with water. In one embodiment, the reconstituted aqueous solution is stable at room temperature for up to about 24 hours upon reconstitution. In one embodiment, the reconstituted aqueous solution is stable at room temperature from about 1-24, 2-20, 2-15, 2-10 hours upon reconstitution. In one embodiment, the reconstituted aqueous solution is stable at room temperature for up to about 20, 15, 12, 10, 8, 6, 4 or 2 hours upon reconstitution. In certain embodiments, the lyophilized formulations upon reconstitution have a pH of about 4 to 5.

In certain embodiment, the lyophilized formulations comprise a compound provided herein (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof), a buffer and a bulking agent.

In one embodiment, the lyophilized formulation comprises about 0.1-2% comprise a compound provided herein (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof), about 1-15% buffer and about 70-95% bulking agent based on the total weight of the lyophilized formulation.

In certain embodiments, a lyophilized formulation comprises a compound provided herein (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) in about 0.1 to about 2% based on the total weight of the lyophilized formulation. In some embodiments, a lyophilized formulation comprises a compound provided herein (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) in an amount of about 0.1 mg to about 5 mg in a vial, for example, a 20 ml vial.

In certain embodiments, a lyophilized formulation comprises a citrate buffer in an amount from about 5% to about 25% based on total weight of the lyophilized formulation. In one embodiment, the citrate buffer comprises anhydrous citric acid and anhydrous sodium citrate.

In some embodiments, the bulking agent in the lyophilized formulations comprises Captisol®, mannitol or Kleptose®, for example, β-cyclodextrin, hydroxypropyl β-cyclodextrin and methylated β-cyclodextrin.

The lyophilized formulation can be reconstituted for parenteral administration to a patient using any pharmaceutically acceptable diluent. Such diluents include, but are not limited to, Sterile Water for Injection (SWFI), Dextrose 5% in Water (D5W), or a cosolvent system. Any quantity of diluent may be used to reconstitute the lyophilized formulation such that a suitable solution for injection is prepared. Accordingly, the quantity of the diluent must be sufficient to dissolve the lyophilized formulation. In one embodiment, 1-5 mL or 1-3 mL of a diluent are used to reconstitute the lyophilized formulation to yield a final concentration of about 0.1-5 mg/mL, about 0.1-1 mg/mL, or about 0.5-1 mg/mL of a compound provided herein, e.g., lenalidomide or a stereoisomer or a mixture of stereoisomers, tautomer, pharmaceutically acceptable salt, solvate, isotopologue, prodrug, hydrate, co-crystal, clathrate, or a polymorph thereof. In certain embodiments, the final concentration of a compound provided herein (e.g., lenalidomide, or a stereoisomer or a mixture of stereoisomers, tautomer, pharmaceutically acceptable salt, solvate, isotopologue, prodrug, hydrate, co-crystal, clathrate, or a polymorph thereof) in the reconstituted solution is about 0.5 mg/mL. In certain embodiment, the volume of the reconstitution diluent varies between 2 ml and 20 ml to yield a final concentration of 0.05-0.5 mg/mL. In certain embodiment, depending on the required dose, multiple vials may be used for reconstitution.

Active ingredients provided herein can be administered by controlled release means or by delivery devices that are well known to those of ordinary skill in the art. Examples include, but are not limited to, those described in U.S. Pat. Nos. 3,845,770, 3,916,899, 3,536,809, 3,598,123, 4,008, 719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500, and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side effects (e.g., adverse effects).

Most controlled-release formulations are designed to initially release an amount of drug (active ingredient) that promptly produces the desired therapeutic effect, then to gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, other physiological conditions, or compounds.

In certain embodiments, the agent may be administered using intravenous infusion, an implantable osmotic pump, a transdermal patch, liposomes, or other modes of administration. In one embodiment, a pump may be used. See, Sefton, *CRC Crit. Ref. Biomed. Eng.* 1987, 14:201-240; Buchwald et al., *Surgery* 1980, 88:507-516; Saudek et al., *N. Engl. J. Med.* 1989, 321:574-579. In another embodiment, polymeric materials can be used. In yet another embodiment, a controlled release system can be placed in proximity of the therapeutic target, thus requiring only a fraction of the systemic dose. See, e.g., Goodson, *Medical Applications of Controlled Release*, vol. 2, pp. 115-138 (1984).

In some embodiments, a controlled release device is introduced into a subject in proximity of the site of inappropriate immune activation or a tumor. Other controlled release systems are discussed in the review by Langer (*Science* 1990, 249:1527-1533). The active ingredient can be dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate). In some embodiments, the inner matrix is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene, propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer). In certain embodiments, the outer polymeric membrane is insoluble in body fluids. The active ingredient then diffuses through the outer polymeric membrane in a release rate controlling step. The percentage of active ingredient contained in such parenteral compositions depends on the specific nature thereof, as well as the needs of the subject.

The compounds provided herein, or pharmaceutically acceptable salts thereof, may also be formulated to target a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLVs) may be formed by drying down egg phosphatidyl choline and brain phosphatidyl serine (7:3 molar ratio) on the inside of a flask. A solution of a compound provided herein in phosphate buffered saline (PBS) lacking divalent cations is added, and the flask is shaken until the lipid film is dispersed. The resulting vesicles are washed to remove unencapsulated compound, pelleted by centrifugation, and then resuspended in PBS.

The compounds or pharmaceutically acceptable salts can be packaged as articles of manufacture containing packaging material, a compound or pharmaceutically acceptable salt thereof provided herein, which is used for treatment, prevention, or amelioration of one or more symptoms or progression of cancer, including solid cancers and blood borne tumors, and a label indicating that the compound or pharmaceutically acceptable salt thereof is used for treatment, prevention, or amelioration of one or more symptoms or progression of cancer, including solid cancers and blood borne tumors.

The articles of manufacture provided herein contain packaging materials. Packaging materials for use in packaging pharmaceutical products are well known to those of skill in the art. See, e.g., U.S. Pat. Nos. 5,323,907, 5,052,558, and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

5.7 Biological Samples

In certain embodiments, the various methods provided herein use samples (e.g., biological samples) from DLBCL patients. The patient can be male or female, and can be an adult, child or infant. Samples can be analyzed at a time during an active phase of DLBCL, or when DLBCL is inactive. In one embodiment, a sample is obtained from a patient prior, concurrently with and/or subsequent to administration of a drug described herein. In a specific embodiment, a sample is obtained from a patient prior to administration of a drug described herein. In certain embodiments, more than one sample from a patient can be obtained.

In certain embodiments, the sample used in the methods provided herein comprises body fluids from a subject. Non-limiting examples of body fluids include blood (e.g., peripheral whole blood, peripheral blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids, including cerebrospinal fluid surrounding the brain and the spinal cord, synovial fluid surrounding bone joints, intracellular fluid is the fluid inside cells, and vitreous humour the fluids in the eyeball. In some embodiments, the sample is a blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Subpopulations of white blood cells, e.g. mononuclear cells, B cells, T cells, monocytes, granulocytes or lymphocytes, can be further isolated using conventional techniques, e.g. magnetically activated cell sorting (MACS) (Miltenyi Biotec, Auburn, California) or fluorescently activated cell sorting (FACS) (Becton Dickinson, San Jose, California).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. In a specific embodiment, the sample used in the methods described herein comprises a tumor biopsy. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the patient receiving a treatment for DLBCL. In another embodiment, the sample is obtained from the patient during the subject receiving a treatment for the DLBCL. In another embodiment, the sample is obtained from the patient after the patient received a treatment for the DLBCL. In various embodiments, the treatment comprises administering a compound described herein (e.g., lenalidomide) to the subject.

In certain embodiments, the sample used in the methods provided herein comprises a plurality of cells. Such cells can include any type of cells, e.g., stem cells, blood cells (e.g., peripheral blood mononuclear cells), lymphocytes, B cells, T cells, monocytes, granulocytes, immune cells, or tumor or cancer cells. The tumor or cancer cells or a tumor tissue, such as a tumor biopsy or a tumor explants. T cells (T lymphocytes) include, for example, helper T cells (effector T cells or Th cells), cytotoxic T cells (CTLs), memory T cells, and regulatory T cells. In one embodiment, the cells used in the methods provided herein are $CD3^+$ T cells, e.g., as detected by flow cytometry. The number of T cells used in the methods can range from a single cell to about $10^9$ cells. B cells (B lymphocytes) include, for example, plasma B cells, dendritic cells, memory B cells, B1 cells, B2 cells, marginal-zone B cells, and follicular B cells. B cells can express immunoglobulins (antibodies, B cell receptor).

Specific cell populations can be obtained using a combination of commercially available antibodies (e.g., Quest Diagnostic (San Juan Capistrano, Calif.); Dako (Denmark)).

In certain embodiments, the sample used in the methods provided herein is from a diseased tissue from a DLBCL patient. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimenta-

5.8 Methods for Detecting Expression Levels

In some embodiments, the methods provided here comprise measuring the expression levels of certain proteins including CD10, Bcl-6, MUM1, and/or FOXP1. The expression levels of CD10, Bcl-6, MUM1, and/or FOXP1 can be determined by known methods in the art.

In some embodiments, the expression levels of CD10, Bcl-6, MUM1, and/or FOXP1 are determined by measuring the mRNA levels of these proteins. Several methods of detecting or quantitating mRNA levels are known in the art. Exemplary methods include but are not limited to northern blots, ribonuclease protection assays, PCR-based methods, and the like. The mRNA sequence can be used to prepare a probe that is at least partially complementary. The probe can then be used to detect the mRNA sequence in a sample, using any suitable assay, such as PCR-based methods, Northern blotting, a dipstick assay, and the like.

In other embodiments, a nucleic acid assay for testing for immunomodulatory activity in a biological sample can be prepared. An assay typically contains a solid support and at least one nucleic acid contacting the support, where the nucleic acid corresponds to at least a portion of an mRNA of CD10, Bcl-6, MUM1, or FOXP1. The assay can also have a means for detecting the altered expression of the mRNA in the sample.

The assay method can be varied depending on the type of mRNA information desired. Exemplary methods include but are not limited to Northern blots and PCR-based methods (e.g., RT-qPCR). Methods such as RT-qPCR can also accurately quantitate the amount of the mRNA in a sample.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to follow the expression of the genes of CD10, Bcl-6, MUM1, and/or FOXP1. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, Real-Time Reverse Transcription-PCR (RT-qPCR) can be used for both the detection and quantification of RNA targets (Bustin, et al., 2005, *Clin. Sci.*, 109:365-379). Quantitative results obtained by RT-qPCR are generally more informative than qualitative data. Thus, in some embodiments, RT-qPCR-based assays can be useful to measure mRNA levels during cell-based assays. The RT-qPCR method is also useful to monitor patient therapy. Examples of RT-qPCR-based methods can be found, for example, in U.S. Pat. No. 7,101,663, which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as the Applied Biosystems 7500, are available commercially, as are the reagents, such as TaqMan Sequence Detection chemistry. For example, TaqMan® Gene Expression Assays can be used, following the manufacturer's instructions. These kits are pre-formulated gene expression assays for rapid, reliable detection and quantification of human, mouse and rat mRNA transcripts. An exemplary PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

Techniques known to one skilled in the art may be used to measure the amount of an RNA transcript(s). In some embodiments, the amount of one, two, three, four, five or more RNA transcripts is measured using deep sequencing, such as ILLUMINA® RNASeq, ILLUMINA® next generation sequencing (NGS), ION TORRENT' RNA next generation sequencing, 454™ pyrosequencing, or Sequencing by Oligo Ligation Detection (SOLID™). In other embodiments, the amount of multiple RNA transcripts is measured using a microarray and/or gene chip. In certain embodiments, the amount of one, two, three or more RNA transcripts is determined by RT-PCR. In other embodiments, the amount of one, two, three or more RNA transcripts is measured by RT-qPCR. Techniques for conducting these assays are known to one skilled in the art. In yet other embodiments, NanoString (e.g., nCounter® miRNA Expression Assays provided by NanoString® Technologies) is used for analyzing RNA transcripts.

In other embodiments, the expression levels of CD10, Bcl-6, MUM1, and/or FOXP1 are determined by measuring the protein levels of CD10, Bcl-6, MUM1, and/or FOXP1. Several protein detection and quantitation methods can be used to measure the level of proteins. Any suitable protein quantitation method can be used. In some embodiments, antibody-based methods are used. Exemplary methods that can be used include but are not limited to immunoblotting (western blot), enzyme-linked immunosorbent assay (ELISA), immunohistochemistry, flow cytometry, cytometric bead array, mass spectroscopy, and the like. Several types of ELISA are commonly used, including direct ELISA, indirect ELISA, and sandwich ELISA.

In a specific embodiment, the protein level is determined by immunohistochemistry (IHC). IHC refers to a lab test that uses antibodies to test for certain antigens (markers) in a sample of tissue, and is a process of detecting antigens (e.g., proteins) in cells of a tissue section by exploiting the principle of antibodies binding specifically to antigens in biological tissues. The antibodies are usually linked to an enzyme or a fluorescent dye. Typically, when the antibodies bind to the antigen in the tissue sample, the enzyme or dye is activated, and the antigen can then be seen under a microscope. IHC can be used to help diagnose diseases, such as cancer. It may also be used to help tell the difference between different types of cancer. IHC can be used to image discrete components in tissues by using appropriately-labeled antibodies to bind specifically to their target antigens in situ. IHC makes it possible to visualize and document the high-resolution distribution and localization of specific cellular components within cells and within their proper histological context. While there are multiple approaches and permutations in IHC methodology, all of the steps involved can be generally separated into two groups: sample preparation and sample staining. In some embodiments, IHC is based on the immunostaining of thin sections of tissues attached to individual glass slides. Multiple small sections can be arranged on a single slide for comparative analysis, a format referred to as a tissue microarray. In other embodiments, IHC is performed by using high-throughput sample preparation and staining.

Samples can be viewed by either light or fluorescence microscopy. In some embodiments, antigen detection in tissue can be performed using an antibody conjugated to an enzyme (horseradish peroxidase) and utilized a colorimetric substrate that could be detected by light microscopy.

In some embodiments, the sample (e.g., a tissue from the patient) has been snap frozen in liquid nitrogen, isopentane or dry ice. In other embodiments, the sample (e.g., a tissue from the patient) has been fixed in formaldehyde and embedded in paraffin wax (FFPE). In both of the above-mentioned methods, the tissue or sections of the tissue can be mounted on slides prior to staining. In yet other embodiments, the IHC-free-floating technique may be used, where the entire IHC procedure is performed in liquid to increase antibody binding and penetration and slide mounting only takes place upon experimental completion. IHC-free-floating appears to be most popular in neuroscience research. When analysis of the tissue by electron microscopy is desired, the tissue can be embedded in acrylate resins such as glycol methacrylate (GMA), a technique referred to as IHC-resin.

In a specific embodiment, IHC can be performed using the method described in the Examples section below.

5.9 Kits

In one aspect, provided herein is a kit of predicting if a subject has an Activated B Cell-like (ABC) subtype of Diffuse Large B-Cell Lymphoma (DLBCL), comprising agents for measuring the expression levels of CD10, Bcl-6, MUM1, and/or FOXP1 in a sample. In some embodiments, the kit further comprises an agent (or tool) for taking a sample from a subject. In some embodiments, the kit further comprises an instruction on how to interpret or use the expression levels determined to predict if a patient has a particular subtype of DLBCL.

In certain embodiments, a kit comprises a reagent or reagents necessary for carrying out an assay(s) described herein, in one or more other containers. In certain embodiments, the kit comprises a solid support, and a means for detecting the RNA or protein expression of at least one biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide.

In a specific embodiment, the kit comprises, in one or more containers, components for conducting RT-PCR, RT-qPCR, deep sequencing, or a microarray such as NanoString assay. In some embodiments, the kit comprises a solid support, nucleic acids contacting the support, where the nucleic acids are complementary to at least 10, 20, 50, 100, 200, 350, or more bases of mRNA, and a means for detecting the expression of the mRNA in a biological sample.

In another specific embodiment, the kit comprises, in one or more containers, components for conducting assays that can determine one or more protein levels, such flow cytometry, ELISA, or HIC.

Such kits may comprise materials and reagents required for measuring RNA or protein. In some embodiments, such kits include microarrays, wherein the microarray is comprised of oligonucleotides and/or DNA and/or RNA fragments which hybridize to one or more of CD10, Bcl-6, MUM1, and/or FOXP1. In some embodiments, such kits may include primers for PCR of either the RNA product or the cDNA copy of the RNA product of the genes or subset of genes, or both. In some embodiments, such kits may include primers for PCR as well as probes for Quantitative PCR. In some embodiments, such kits may include multiple primers and multiple probes wherein some of said probes have different flourophores so as to permit multiplexing of multiple products of a gene product or multiple gene products. In some embodiments, such kits may further include materials and reagents for creating cDNA from RNA. In some embodiments, such kits may include antibodies specific for CD10, Bcl-6, MUM1, and/or FOXP1. Such kits may additionally comprise materials and reagents for isolating RNA and/or proteins from a biological sample. In addition, such kits may include materials and reagents for synthesizing cDNA from RNA isolated from a biological sample. In some embodiments, such kits may include, a computer program product embedded on computer readable media for predicting whether a patient is responsive to a compound as described herein. In some embodiments, the kits may include a computer program product embedded on a computer readable media along with instructions.

For antibody based kits, the kit can comprise, for example: (1) a first antibody (which may or may not be attached to a solid support) which binds to a peptide, polypeptide or protein of interest; and, optionally, (2) a second, different antibody which binds to either the peptide, polypeptide or protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for predicting whether a DLBCL patient is a patient having the ABC subtype of DLBCL.

In certain embodiments of the methods and kits provided herein, solid phase supports are used for purifying proteins, labeling samples, or carrying out the solid phase assays. Examples of solid phases suitable for carrying out the methods disclosed herein include beads, particles, colloids, single surfaces, tubes, multi-well plates, microtiter plates, slides, membranes, gels, and electrodes. When the solid phase is a particulate material (e.g., a bead), it is, in one embodiment, distributed in the wells of multi-well plates to allow for parallel processing of the solid phase supports.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

Certain embodiments of the invention are illustrated by the following non-limiting examples.

6. EXAMPLES

The examples below are carried out using standard techniques, which are well known and routine to those of skill in the art, except where otherwise described in detail. The examples are intended to be merely illustrative.

This study performed IHC analyses on 8 DLBCL markers to determine if a computational algorithm can be derived to identify ABC tumors that would be comparable to gene expression profiling (GEP) results. A total of 200 cases of DLBCL (including core needle biopsies and excisional biopsies) were obtained (Avaden Bio, Seattle WA). Among them, 100 samples were randomly selected as a training set for testing of 8 validated IHC assays. The IHC assay results were then compared to the Nanostring's Lymph2Cx assay results. A new IHC algorithm was proposed to identify ABC tumors either alone or in combination with the Hans algorithm. The proposed algorithms were validated in independent 100 DLBCL samples and the performance of the IHC assays were compared to the Nanostring's Lymph2Cx assay results in the validation set.

Materials and Methods

DLBCL samples. A total of 200 cases of DLBCL (including core needle biopsies and excisional biopsies) were obtained for the study (Avaden Biosciences, Seattle, WA). Among them, 100 samples were selected as a training set. The remaining 100 samples from were used as a validation set. Patient characteristics of the DLBCL samples between the training set and the validation set are summarized in Table 1.

TABLE 1

Patient and tumor characteristics of training and validations sets

| Characteristic | Training cohort (n = 100) | Validation cohort (n = 100) | P value* |
|---|---|---|---|
| Age - median (range) | 67 (18-98) | 68 (23-91) | — |
| Gender - n (%) | | | |
| Male | 58 (58%) | 58 (58%) | 1.00 |
| Female | 42 (42%) | 42 (42%) | |
| Tissue Type - n (%) | | | |
| Nodal | 36 (36%) | 27 (27%) | 0.04 |
| Extra-nodal | 64 (64%) | 73 (73%) | |
| GEP result - n (%) | | | |
| ABC | 27 (27%) | 37 (37%) | |
| GCB | 60 (60%) | 50 (50%) | 0.19 |
| Unclassified | 12 (12%) | 12 (12%) | |
| No test | 1 (1%) | 1 (1%) | |

*P values were derived from Chi-squared test to assess the variables between the training and the validation sets.

Immunohistochemistry.

For each sample, multiple 5 μm thick slides were prepared and a single slide was stained with hematoxylin and eosin and reviewed by the pathologist to define the tumor area.

The remaining slides were then subjected to standard immunohistochemical procedures including antigen retrieval, incubation with antibodies, detection reagents and staining reagents per each laboratory's standard operating procedures for the respective LDT. For each of the training samples, the following IHC tests were performed: CD20, CD10, Bcl-6, MUM1, FOXP1, Bcl-2, Ki-67 and CD5 by Neogenomics. For the validation set, the following IHC tests were performed CD20, CD10, BCL6, MUM1 and FOXP1. For the validation set, two laboratories (Neogenomics and PPD) were chosen to challenge the robustness of the algorithms. (Neogenomics and PPD) using their respective independently developed laboratory tests. The antibody clones used by each of the laboratories for IHC assays are listed in Table 2. Blocking, amplification and 3'-diaminobenzidine detection kits were used according to manufacturer's instructions (Ventana, Leica). The immunostaining was performed per testing lab's protocols on either Benchmark XT (Ventana), Benchmark Ultra (Ventana), or Bond III (Leica) instruments. Each of the IHC assays in the study were validated with proper positive and negative controls in the testing labs.

For each IHC antibody stain, percentage of positive stained tumor cells in 5% increments (or <1%) and staining intensity (0, 1+, 2+ and 3+) in each DLBCL sample were scored. For the training set, scoring was estimated visually by three pathologists trained on Neogenomics LDTs who were blinded to GEP results to allow for inter-reader reproducibility to be assessed. The IHC scores were tabulated on a spreadsheet using Microsoft Office Excel. The scoring of the training set was provided independently by three independent pathologists. The scoring of the validation set was provided independently by two pathologists at each institution (n=4).

predictive score that assigned the sample into one of the 3 classes: ABC, GCB or Unclassified. Experimentally, 5 of 5 µm sections were prepared from each of the FFPE tissue blocks. An RNA input of 200 ng per sample was used to carry out Lymph2Cx COO Assay (NanoString, WA).

Construction and Validation of the New IHC Algorithm.

Percentages of positively stained cells for the samples of the training set were tabulated on a spreadsheet alongside with corresponding GEP calls from Lymph2Cx COO Assay. Five of the 8 IHC stain results including CD20, CD10, Bcl-6, MUM1 or FOXP1 demonstrated abilities to discriminate ABC from non-ABC tumors and concordance when compared to the GEP calls. We then focused on combinations of these IHC stains that could achieve high sensitivity and high specificity for predicting the ABC subtype.

Figure 1:
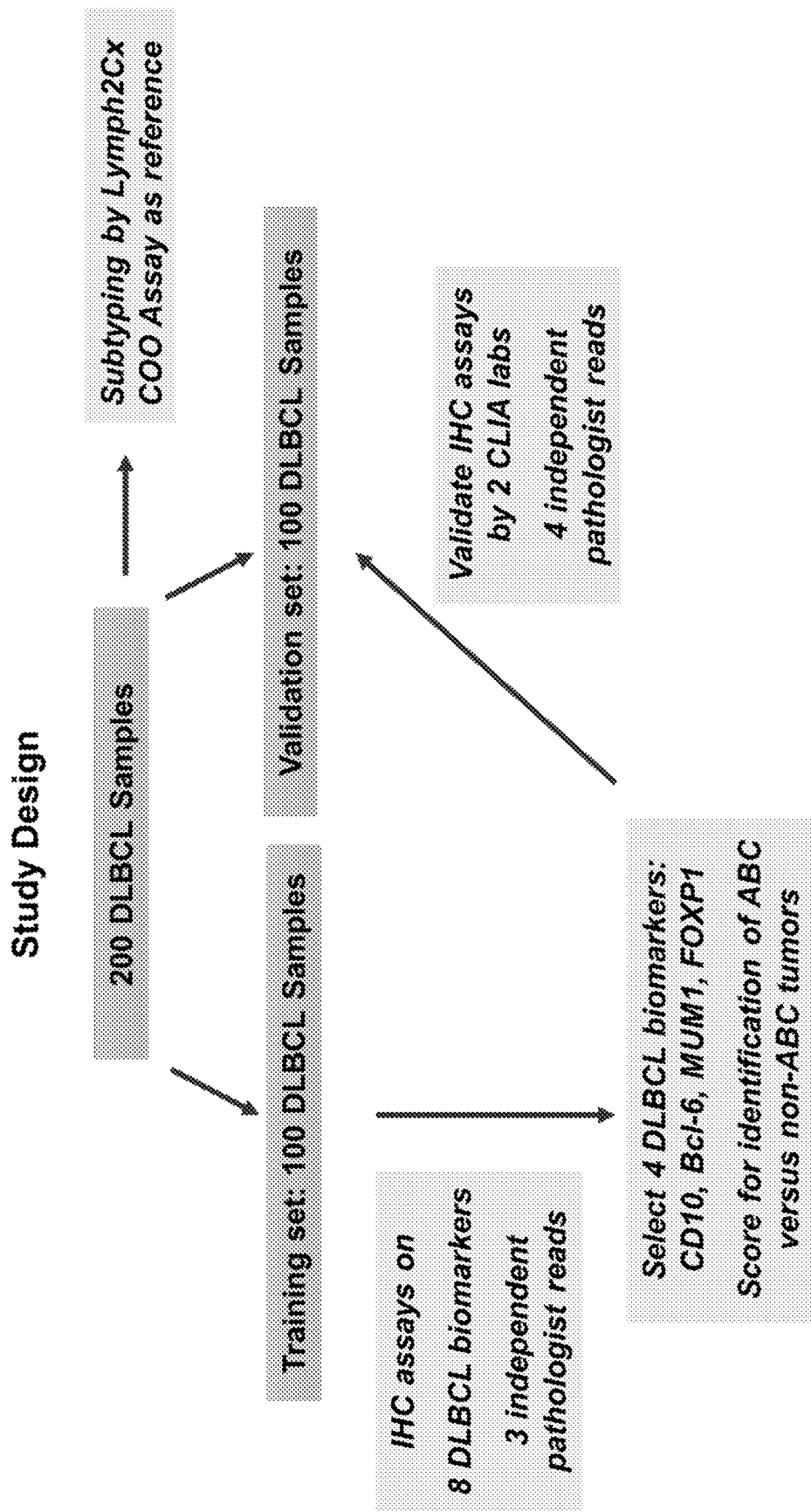
FIG. 1 depicts the workflow of the study design in the Example section.

Two algorithms involving 4 IHC stains were proposed to discriminate ABC vs. non-ABC tumors of DLBCL from the analysis of the training set (see FIG. 1, FIG. 2A, and FIG. 2B). One algorithm has a composite score based on sum of weighted percentage of positively stained cells of 4 IHC markers: CD10, Bcl-6, MUM1 and FOXP1; the other applies the Hans algorithm first and then the newly proposed algorithm to the non-GCB samples of the Hans result.

The IHC assays and Lymph2Cx COO assay were then performed on the 100 independent DLBCL samples of the validation set. The pre-determined algorithms including the cutoffs were computed based on the IHC stains of the validation set to determine their abilities to predict ABC and non-ABC tumors. The predicted IHC calls were compared to the Lymph2Cx COO assay calls to evaluate the performance of the algorithms.

Statistical Analysis.

The $\chi2$ test was used to compare patient characteristics between the training and the validation sets. The COO calls

TABLE 2

Antibodies and instruments for IHC assays

A. Training set (Neogenomics)

| Antibody | Clone | Manufacturer | Catalogue # |
|---|---|---|---|
| CD20 | L26 | Leica | NCL-L-CD20-L26 |
| CD10 | 56C6 | Leica | NCL-L-CD10-270 |
| BCL6 | LN22 | Leica | NCL-L-Bcl-6-564 |
| MUM1 | MUM1p | Dako | M7259 |
| FOXP1 | JC12 | Novus | NB100-65125 |
| BCL2 | 124 | Dako | M0887 |
| Ki-67 | MIB-1 | BioCare | PM362DASS |
| CD5 | 4C7 | Leica | NCL-L-CD5-4C7 |

B. Validation set (Neogenomics and PPD)

| | Neogenomics Lab | | | PPD Lab | | |
|---|---|---|---|---|---|---|
| Antibody | Clone | Company | Catalogue # | Clone | Company | Catalogue # |
| CD20 | L26 | Leica | NCL-L-CD20-L26 | L26 | Ventana | 760-2531 |
| CD10 | 56C6 | Leica | NCL-L-CD10-270 | SP67 | Ventana | 790-4506 |
| BCL6 | LN22 | Leica | NCL-L-Bcl-6-564 | GI91E | Ventana | 760-4241 |
| FOXP1 | JC12 | Novus | NB100-65125 | SP133 | Ventana | 760-4611 |
| MUM1 | MUM1p | Dako | M7259 | MUM1p | Dako | M7259 |

Lymph2Cx COO Assay.

GEP was used as a reference method and performed by using Lymph2Cx COO Assay developed and analytically validated by NanoString (8). Lymph2Cx COO Assay includes a set of 15 COO genes and 5 "housekeeping" genes that had low variability across samples. A weighted average expression of the 15 COO genes was used to generate a made by the IHC algorithms were compared to the subtypes as classified by the Lymph2Cx COO assay to determine accuracy of the IHC algorithms in 2×2 table. Each pathologist's results were evaluated individually and then together. Concordance between the IHC calls from different pathologists were calculated. Concordance between the IHC calls and the GEP calls (for ABCs and non-ABCs, excluding GEP unclassified subtype) were calculated for the proposed algorithm. Acceptance criteria was set at >80% concordance (ABC and GCB) for at least one of the laboratories between IHC and GEP for the validation of each of the algorithms. The protocol was written such that a ≥80% concordance between IHC and GEP for the validation set in both testing labs validates the algorithm across different labs and different IHC assays and platforms.

|  | GEP ABC | GEP GCB |
|---|---|---|
| IHC ABC | a | b |
| IHC non-ABC | c | d |

Overall Percentage Agreement (OPA) = (a + d)/(a + b + c + d) × 100%

Results

Patient Characteristics of the Training and Validation Sets.

The training set included 58% males and 42% females with a median age of 67 years (range, 18-98 years). The validation set comprised 58% males and 42% females with a median age of 68 years (range, 23-91 years). The characteristics of the patients were not significantly different (Table 1). For the training set, 27 cases were classified into ABCs, 60 cases into GCBs and 12 cases into unclassified by GEP; and for the validation set, 37 cases were classified into ABCs, 50 cases into GCBs and 12 cases into unclassified by GEP. The classification of the patient cases with GEP-defined ABC, GCB and unclassified subtypes were also not significantly different between the training and the validation set (Table 1).

Reproducibility of Inter-Reader Evaluation and Inter-Laboratory Testing on IHC Assays.

One-hundred cases of DLBCL in the training set were tested in a single lab with the 8 IHC assays (Table 2), and the IHC stains were evaluated by 3 independent pathologists. The inter-pathologist variability was assessed by pair-wise concordance for each of the IHC assays individually used for the Hans and the new IHC algorithms ranged from 83% to 93%. The average concordance of the pathologists' calls on the Hans algorithm is 90% (Table 3). One-hundred cases of DLBCL in the validation set were tested in 2 independent labs with 4 selected IHC assays. The labs used different antibody clones and instruments for some of the IHC assays (Table 2). In addition, The IHC stains of the validation set were evaluated by 4 independent pathologists (2 pathologists per lab). The average pair-wise concordance between the pathologists of the individual IHC assays for the validation set ranged from 76% to 93% (Table 3). The average pair-wise concordance of the pathologists' calls on the Hans algorithm and the new IHC algorithm are 80% and 86%, respectively (Table 3).

TABLE 3

Concordance of pathologist evaluation of IHC assays

| Assay/algorithm | Average concordance from pair-wise comparisons (Training Set, 3 pathologists) | Average concordance from pair-wise comparisons (Validation Set, 2 labs, 4 pathologists) |
|---|---|---|
| CD10 | 93% | 93% |
| BCL6 | 83% | 76% |
| MUM1 | 84% | 85% |
| FOXP1 | 92% | 92% |
| Hans Algorithm | 90% | 86% |
| New IHC Algorithm | —* | 86% |

*Not included for training set

A New IHC Algorithm for Classification of DLBCL.

In the training set of 100 DLBCL cases, the use of the Lymph2Cx COO Assay resulted in 27 ABCs, 60 GCB and 12 unclassified calls (1 no call). The Hans algorithm classified 47 cases of GCB, and 53 of non-GCB. 73% GEP-defined GCB cases were classified as GCBs and 100% GEP-defined ABC cases were classified as non-GCBs by the Hans' algorithm. The overall percentage agreement (71/87) between the Hans algorithm and the GEP result is 82%.

Various combinations of the 8 IHC assays were tested to separate the cases into ABC and non-ABC subtypes according to the GEP result of the training set. The new IHC algorithm calculated on 4 IHC stains of CD10, Bcl-6, MUMP1 and FOXP1 was identified to achieve the highest possible concordance with the GEP classification on ABCs. Although the new algorithm was developed based on the first pathologist's evaluation of the IHC stains of the training set, the classification results are highly concordant (88%) among the 3 pathologists' evaluation (see Table 3).

Validation of the New IHC Algorithm for Classification of DLBCL.

The performance of the new IHC algorithm, either alone or in combination with the Hans algorithm, was evaluated in the 100 independent cases in the validation set. Each of the cases were assigned to of GEP-defined ABC, GBC or unclassified subtype according to the Lymph2Cx COO assay. The concordance of the IHC calls by the new IHC algorithm to the GEP calls are shown in Table 4.

The percentage agreement of the ABC calls ranged from 81% to 91% among the 4 pathologists' evaluation. The overall percentage agreement ranged from 79% to 86% among the 4 pathologists' evaluation. (Table 4).

TABLE 4

Comparison of classification results between new IHC algorithm versus GEP in validation set Pathologist 1: 98 samples: 37 ABC, 49 GCB, 12 unclassified by GEP. 2 no call.

| | GEP | |
|---|---|---|
| New IHC Algorithm | ABC (n = 37) | GCB (n = 49) |
| ABC (%) | 30/37 (81%) | |
| Non-ABC (%) | | 41/49 (84%) |
| Overall Accuracy (%) | 71/86 (83%) | |

Pathologist 2: samples: 36 ABC, 49 GCB, 12 unclassified by GEP. 3 no call.

| | GEP | |
|---|---|---|
| New IHC Algorithm | ABC (n = 36) | GCB (n = 49) |
| ABC (%) | 29/36 (81%) | |
| Non-ABC (%) | | 43/49 (88%) |
| Overall Accuracy (%) | 72/85 (85%) | |

TABLE 4-continued

Comparison of classification results between new
IHC algorithm versus GEP in validation set Pathologist 3: 94 samples: 35 ABC, 48
GCB, 11 unclassified by GEP. 6 no call.

| New IHC Algorithm | GEP | |
|---|---|---|
| | ABC (n = 35) | GCB (n = 48) |
| ABC (%) | 32/35 (91%) | |
| Non-ABC (%) | | 39/48 (81%) |
| Overall Accuracy (%) | 71/83 (86%) | |

Pathologist 4: 92 samples: 32 ABC, 48
GCB, 12 unclassified by GEP. 8 no call.

| New IHC Algorithm | GEP | |
|---|---|---|
| | ABC (n = 32) | GCB (n = 48) |
| ABC (%) | 26/32 (81%) | |
| Non-ABC (%) | | 37/48 (77%) |
| Overall Accuracy (%) | 63/80 (79%) | |

Further, the new IHC algorithm was applied in conjunction with the Hans algorithm. The concordance of the IHC calls by the Hans and the new IHC algorithms to the GEP calls are shown in Table 5. The percentage agreement of the ABC calls ranged from 92% to 97% among the 4 pathologists' evaluation using 2 independently derived sets of LDT tests (2 pathologists per set of LDT tests). The overall percentage agreement ranged from 84% to 88% among the 4 pathologists' evaluation. (Table 5).

TABLE 5

Comparison of classification results between Hans algorithm
plus new IHC algorithm versus GEP in validation set Pathologist 1: 98 samples: 37 ABC, 49
GCB, 12 unclassified by GEP. 2 no call.

| Hans + New IHC Algorithm | GEP | |
|---|---|---|
| | ABC (n = 37) | GCB (n = 49) |
| ABC (%) | 34/37 (92%) | |
| Non-ABC (%) | | 42/49 (86%) |
| Overall Accuracy (%) | 76/86 (88%) | |

Pathologist 2: samples: 36 ABC, 49
GCB, 12 unclassified by GEP. 3 no call.

| Hans + New IHC Algorithm | GEP | |
|---|---|---|
| | ABC (n = 36) | GCB (n = 49) |
| ABC (%) | 32/36 (89%) | |
| Non-ABC (%) | | 44/49 (90%) |
| Overall Accuracy (%) | 76/85 (89%) | |

Pathologist 3: 94 samples: 35 ABC, 48
GCB, 11 unclassified by GEP. 6 no call.

| Hans + New IHC Algorithm | GEP | |
|---|---|---|
| | ABC (n = 35) | GCB (n = 48) |
| ABC (%) | 34/35 (97%) | |
| Non-ABC (%) | | 39/48 (81%) |
| Overall Accuracy (%) | 73/83 (88%) | |

Pathologist 4: 92 samples: 32 ABC, 48
GCB, 12 unclassified by GEP, 8 no call.

| Hans + New IHC Algorithm | GEP | |
|---|---|---|
| | ABC (n = 32) | GCB (n = 48) |
| ABC (%) | 30/32 (94%) | |
| Non-ABC (%) | | 37/48 (77%) |
| Overall Accuracy (%) | 67/80 (84%) | |

The agreement of the ABC calls ranged from 92% to 97% among the 4 pathologists' evaluation. The overall percentage agreement ranged from 84% to 88% among the 4 pathologists' evaluation (see Table 5).

In the study, no single IHC antibody has been sufficient in classifying DLBCL. For this reason, combinations of antibodies and algorithms have been developed based on concordance with the classification of DLBCL by GEP. The Hans algorithm is highly useful to determine GCB subtype of DLBCL. Apart from the Hans' algorithm, several other IHC stain algorithms have been proposed to classify subtypes of DLBCL. However, little data has been found in identification of ABC versus non-ABC tumors as compared to GEP. IHC assays can not only provide information similar to that obtained by GEP but also be performed on archival FFPE tumor tissues routinely in most pathology laboratories, making the testing practical for widespread clinical use. The proposed IHC algorithm demonstrates a potential ability to predict the ABC subtype of DLBCL tumors. The results of this study should allow laboratories with limited molecular expertise to choose the method for their clinical practice. It is evidently sufficient to allow cell of origin determination for therapy choice, especially for therapies targeting ABC subtype of DLBCL.

The new algorithm places less weight on some GC-specific markers and more ABC-specific markers such as FOXP1 in the algorithm to complement the markers in the Hans' algorithm. FOXP1 gene is on chromosome 3p14.1 and encodes a member of the FOX family of transcription factors. In this study, we found that the addition of FOXP1 to the algorithm achieved a higher specificity for identification of the ABC tumors.

Although GEP defines about 10-15% of DLBCL cases in to unclassified subtype, we only used GEP-defined ABC and GCB cases to derive the new algorithm in this study. GEP-defined unclassified DLBCL is not a well-characterized biological entity. For example, previous studies have shown that the GEP-defined unclassified DLBCL subtype is similar to the ABC subtype in patient prognosis. Our observations also suggested that if we applied the new IHC algorithm to GEP-defined unclassified cases, the majority of the GEP-unclassified cases would have been assigned into the ABC subtype by the IHC method.

In conclusion, the present disclosure describes a novel IHC method that it closely replicates the GEP based COO classification of DLBCL into the ABC and the non-ABC subtypes. It represents an improvement in using routine clinical IHC assays in DLBCL subtyping. The new method could facilitate future research and clinical development in DLBCL by using archival FFPE tumor materials and evaluation of patients with DLBCL for novel experimental therapies.

Validation of an Alternative IHC Algorithm for Classification of DLBCL.

In addition to the two algorithms depicted in FIG. 2A and FIG. 2B, an alternative algorithm was also tested and validated for discriminating ABC vs. non-ABC tumors of DLBCL. This alternative algorithm also has a composite score based on sum of weighted percentage of positively stained cells of 3 IHC markers: CD10, MUM1 and FOXP1, and this composite score is calculated as follows: Composite Score=$-1.4367173-0.0238081 \times CD10+0.01051371 \times MUM1+0.02111138 \times FOXP1$, wherein CD10 represents the percentage of the positively stained cells determined by the IHC method using an anti-CD10 antibody, MUM1 represents the percentage of the positively stained cells determined by the IHC method using an anti-MUM1 antibody, and FOXP1 represents the percentage of the positively stained cells determined by the IHC method using an anti-FOXP1 antibody. When the composite score is 0 or higher than 0, the tumor is classified as ABC subtype, and when the composite score is lower than 0, the tumor is classified as non-ABC subtype. Similarly, a combination method using this alternative algorithm and Hans algorithm was tested and validated. The method applies the Hans algorithm first and then applies the alternative algorithm only to the non-GCB samples of the Hans result in order to call out ABC samples. Table 6 and Table 7 summarize the results.

TABLE 6

Comparison of classification results between an alternative IHC algorithm versus GEP in validation set Pathologist 1: 98 samples: 37 ABC, 49 GCB, 12 unclassified by GEP. 2 no call.

| | GEP | |
|---|---|---|
| New IHC Algorithm | ABC (n = 37) | GCB (n = 49) |
| ABC (%) | 33/37 (89%) | |
| Non-ABC (%) | | 38/49 (78%) |
| Overall Accuracy (%) | 71/86 (83%) | |

Pathologist 2: 97 samples: 36 ABC, 49 GCB, 12 unclassified by GEP. 3 no call.

| | GEP | |
|---|---|---|
| New IHC Algorithm | ABC (n = 36) | GCB (n = 49) |
| ABC (%) | 28/36 (77%) | |
| Non-ABC (%) | | 41/49 (84%) |
| Overall Accuracy (%) | 69/85 (81%) | | athologist 3: 94 samples: 35 ABC, 48 GCB, 11 unclassified by GEP. 6 no call.

| | GEP | |
|---|---|---|
| New IHC Algorithm | ABC (n = 35) | GCB (n = 48) |
| ABC (%) | 34/35 (97%) | |
| Non-ABC (%) | | 32/48 (67%) |
| Overall Accuracy (%) | 66/83 (80%) | |

Pathologist 4: 92 samples: 32 ABC, 48 GCB, 12 unclassified by GEP. 8 no call.

| | GEP | |
|---|---|---|
| New IHC Algorithm | ABC (n = 32) | GCB (n = 48) |
| ABC (%) | 31/32 (97%) | |
| Non-ABC (%) | | 27/48 (56%) |
| Overall Accuracy (%) | 58/80 (75%) | |

TABLE 7

Comparison of classification results between Hans algorithm plus an alternative IHC algorithm versus GEP in validation set Pathologist 1: 98 samples: 37 ABC, 49 GCB, 12 unclassified by GEP. 2 no call.

| Hans + New IHC | GEP | |
|---|---|---|
| Algorithm | ABC (n = 37) | GCB (n = 49) |
| ABC (%) | 34/37 (92%) | |
| Non-ABC (%) | | 42/49 (86%) |
| Overall Accuracy (%) | 76/86 (88%) | |

Pathologist 2: 97 samples: 36 ABC, 49 GCB, 12 unclassified by GEP. 3 no call.

| Hans + New IHC | GEP | |
|---|---|---|
| Algorithm | ABC (n = 36) | GCB (n = 49) |
| ABC (%) | 30/36 (83%) | |
| Non-ABC (%) | | 44/49 (90%) |
| Overall Accuracy (%) | 74/85 (87%) | |

Pathologist 3: 94 samples: 35 ABC, 48 GCB, 11 unclassified by GEP. 6 no call.

| Hans + New IHC | GEP | |
|---|---|---|
| Algorithm | ABC (n = 35) | GCB (n = 48) |
| ABC (%) | 35/35 (100%) | |
| Non-ABC (%) | | 36/48 (75%) |
| Overall Accuracy (%) | 71/83 (86%) | |

Pathologist 4: 92 samples: 32 ABC, 48 GCB, 12 unclassified by GEP. 8 no call.

| Hans + New IHC | GEP | |
|---|---|---|
| Algorithm | ABC (n = 32) | GCB (n = 48) |
| ABC (%) | 32/32 (100%) | |
| Non-ABC (%) | | 31/48 (65%) |
| Overall Accuracy (%) | 63/80 (79%) | |

Subtype Classifications by the Lymph2Cx Assay and the DxTerity COO Assay

Seventy-five independent DLBCL samples were obtained with patient follow-up data on overall survival and disease recurrence. The FFPE blocks ranging from 2 to 10 years of age were tested by two DLBCL subtyping assays: the Nanostring's Lymph2Cx assay and the DxTerity DLBCL COO assay. Both assays yielded gene expression data with adequate quality. Seventy-four of 75 and 75 of 75 cases designated as a subtype by the Lymph2Cx assay and the DxTerity COO assay, respectively. The subtype classification results including unclassified cases by the Lymph2Cx assay and the DxTerity COO assay are shown in Table 8.

TABLE 8

The subtype classification results including unclassified cases by the Lymph2Cx assay and the DxTerity COO assay.

| Subtype | Nanostring's Lymph2Cx assay (n = 75) | DxTerity DLBCL COO assay (n = 75) |
|---|---|---|
| ABC | 31 (41%) | 36 (48%) |
| GCB | 37 (49%) | 38 (51%) |
| Unclassified | 6 (8%) | 1 (1%) |
| No test | 1 (1%) | 0 (0%) |

The Kaplan-Meier analysis was carried out to determine whether the subtypes of the disease made by the Lymph2Cx assay and the DxTerity COO assay maintained a prognostic significance previously demonstrated in the literature. The Lymph2Cx-defined and the DxTerity COO assay-defined ABC groups both had worse outcome than the GCB groups, which are consistent with the previous reported observations in the literature (FIGS. 3A-3lI and FIGS. 4A-4lI).

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of predicting if a subject has an Activated B Cell-like (ABC) subtype of Diffuse Large B-Cell Lymphoma (DLBCL) or a non-ABC subtype of DLBCL comprising:
   (a) measuring the expression levels of biomarkers consisting of CD10, Bcl-6, MUM1, and FOXP1 in a sample from the subject;
   (b) determining a CD10 percentage being the percentage of the CD10 positively stained cells determined using an anti-CD10 antibody, a Bcl-6 percentage being the percentage of the Bcl-6 positively stained cells determined using an anti-Bcl-6 antibody, a MUM1 percentage being the percentage of the MUM1 positively stained cells determined using an anti-MUM1 antibody, and a FOXP1 percentage being the percentage of the FOXP1 positively stained cells determined by using an anti-FOXP1 antibody;
   (c) determining a composite score according to: the composite score=(−0.5×the CD10 percentage)+(−0.2×the Bcl-6 percentage)+(0.4×the MUM1 percentage)+(0.1×the FOXP1 percentage);
   (d) predicting if the subject has an ABC subtype or a non-ABC subtype of DLBCL based on the composite score; and
   (e) (i) administering to the subject predicted to have the ABC subtype of DLBCL a therapeutically effective amount of a treatment compound suitable for treating the ABC subtype of DLBCL, or (ii) administering to the subject predicted to have the non-ABC subtype of DLBCL a therapeutically effective amount of a treatment compound suitable for treating the non-ABC subtype of DLBCL.

2. The method of claim 1, wherein the expression levels of CD10, Bcl-6, MUM1, and FOXP1 are measured by an immunohistochemistry (IHC) method, and the percentage of the CD10 positively stained cells, the percentage of the Bcl-6 positively stained cells, the percentage of the MUM1 positively stained cells, and the percentage of the FOXP1 positively stained cells are determined by the IHC method.

3. The method of claim 1, wherein the method is used in combination with a second method for predicting if the subject has the ABC subtype of DLBCL or the non-ABC subtype of DLBCL.

4. A method of predicting if a subject has an Activated B Cell-like (ABC) subtype of Diffuse Large B-Cell Lymphoma (DLBCL) or a non-ABC subtype of DLBCL comprising:
   (a) measuring the expression levels of biomarkers consisting of CD10, Bcl-6, MUM1, and FOXP1 in a sample from the subject;
   (b) determining a CD10 percentage being the percentage of the CD10 positively stained cells determined using an anti-CD10 antibody, a Bcl-6 percentage being the percentage of the Bcl-6 positively stained cells determined using an anti-Bcl-6 antibody, a MUM1 percentage being the percentage of the MUM1 positively stained cells determined using an anti-MUM1 antibody, and a FOXP1 percentage being the percentage of the FOXP1 positively stained cells determined by using an anti-FOXP1 antibody;
   (c) determining a composite score according to: the composite score=(a CD10 weight×the CD10 percentage)+(a Bcl-6 weight×the Bcl-6 percentage)+(a MUM1 weight×the MUM1 percentage)+(a FOXP1 weight×the FOXP1 percentage);
   (d) predicting that the subject has the ABC subtype of DLBCL if the composite score is 8 or higher than 8, or predicting that the subject has the non-ABC subtype of DLBCL if the composite score is lower than 8; and
   (e) (i) administering to the subject predicted to have the ABC subtype of DLBCL a therapeutically effective amount of a treatment compound suitable for treating the ABC subtype of DLBCL, or (ii) administering to the subject predicted to have the non-ABC subtype of DLBCL a therapeutically effective amount of a treatment compound suitable for treating the non-ABC subtype of DLBCL.

5. A method of predicting if a subject has an Activated B Cell-like (ABC) subtype of Diffuse Large B-Cell Lymphoma (DLBCL) or a non-ABC subtype of DLBCL comprising:
   (a) measuring the expression levels of biomarkers consisting of CD10, MUM1, and FOXP1 in a sample from the subject;
   (b) determining a CD10 percentage being the percentage of the CD10 positively stained cells determined using an anti-CD10 antibody, a MUM1 percentage being the percentage of the MUM1 positively stained cells determined using an anti-MUM1 antibody, and a FOXP1 percentage being the percentage of the FOXP1 positively stained cells determined by using an anti-FOXP1 antibody;
   (c) determining a composite score according to: the composite score=(−1.4367173)+(−0.0238081×the CD10 percentage)+(0.01051371×the MUM1 percentage)+(0.02111138×the FOXP1 percentage);
   (d) predicting if the subject has an ABC subtype or a non-ABC subtype of DLBCL based on the composite score; and
   (e) (i) administering to the subject predicted to have the ABC subtype of DLBCL a therapeutically effective amount of a treatment compound suitable for treating the ABC subtype of DLBCL, or (ii) administering to the subject predicted to have the non-ABC subtype of DLBCL a therapeutically effective amount of a treatment compound suitable for treating the non-ABC subtype of DLBCL.

6. The method of claim 5, wherein the expression levels of CD10, MUM1, and FOXP1 are measured by an immunohistochemistry (IHC) method, and the percentage of the CD10 positively stained cells, the percentage of the MUM1 positively stained cells, and the percentage of the FOXP1 positively stained cells are determined by the IHC method.

7. The method of claim 5, wherein the method is used in combination with a second method for predicting if the subject has the ABC subtype of DLBCL or the non-ABC subtype of DLBCL.

8. A method of predicting if a subject has an Activated B Cell-like (ABC) subtype of Diffuse Large B-Cell Lymphoma (DLBCL) or a non-ABC subtype of DLBCL comprising:
  (a) measuring the expression levels of biomarkers consisting of CD10, MUM1, and FOXP1 in a sample from the subject;
  (b) determining a CD10 percentage being the percentage of the CD10 positively stained cells determined using an anti-CD10 antibody, a MUM1 percentage being the percentage of the MUM1 positively stained cells determined using an anti-MUM1 antibody, and a FOXP1 percentage being the percentage of the FOXP1 positively stained cells determined by using an anti-FOXP1 antibody;
  (c) determining a composite score according to: the composite score=(a CD10 weight×the CD10 percentage)+(a MUM1 weight×the MUM1 percentage)+(a FOXP1 weight×the FOXP1 percentage);
  (d) predicting that the subject has the ABC subtype of DLBCL if the composite score is 0 or higher than 0, or predicting that the subject has the non-ABC subtype of DLBCL if the composite score is lower than 0; and
  (e) (i) administering to the subject predicted to have the ABC subtype of DLBCL a therapeutically effective amount of a treatment compound suitable for treating the ABC subtype of DLBCL, or (ii) administering to the subject predicted to have the non-ABC subtype of DLBCL a therapeutically effective amount of a treatment compound suitable for treating the non-ABC subtype of DLBCL.

9. The method of claim 1, wherein the subject has DLBCL, and the sample is obtained from a tissue of the subject comprising DLBCL cells.

10. The method of claim 5, wherein the subject has DLBCL, and the sample is obtained from a tissue of the subject comprising DLBCL cells.

11. The method of claim 1, wherein the treatment compound suitable for treating the ABC-subtype of DLBCL comprises lenalidomide or a stereoisomer or a mixture of stereoisomers, tautomer, pharmaceutically acceptable salt, solvate, isotopologue, prodrug, hydrate, co-crystal, clathrate, or a polymorph thereof.

12. The method of claim 5, wherein the treatment compound suitable for treating the ABC-subtype of DLBCL comprises lenalidomide or a stereoisomer or a mixture of stereoisomers, tautomer, pharmaceutically acceptable salt, solvate, isotopologue, prodrug, hydrate, co-crystal, clathrate, or a polymorph thereof.

13. The method of claim 1, comprising predicting that the subject has the ABC subtype of DLBCL if the composite score is 8 or higher than 8, or predicting that the subject has the non-ABC subtype of DLBCL if the composite score is lower than 8.

14. The method of claim 4, wherein the expression levels of CD10, Bcl-6, MUM1, and FOXP1 are measured by an immunohistochemistry (IHC) method, and the percentage of the CD10 positively stained cells, the percentage of the Bcl-6 positively stained cells, the percentage of the MUM1 positively stained cells, and the percentage of the FOXP1 positively stained cells are determined by the IHC method.

15. The method of claim 4, wherein the composite score is determined according to: the composite score=(−0.5×the CD10 percentage)+(−0.2×the Bcl-6 percentage)+(0.4×the MUM1 percentage)+(0.1×the FOXP1 percentage).

16. The method of claim 4, wherein the method is used in combination with a second method for predicting if the subject has the ABC subtype of DLBCL or the non-ABC subtype of DLBCL.

17. The method of claim 4, wherein the subject has DLBCL and the sample is obtained from a tissue of the subject comprising DLBCL cells.

18. The method of claim 4, wherein the treatment compound suitable for treating the ABC-subtype of DLBCL comprises lenalidomide or a stereoisomer or a mixture of stereoisomers, tautomer, pharmaceutically acceptable salt, solvate, isotopologue, prodrug, hydrate, co-crystal, clathrate, or a polymorph thereof.

19. The method of claim 5, comprising predicting that the subject has the ABC subtype of DLBCL if the composite score is 0 or higher than 0, or predicting that the subject has the non-ABC subtype of DLBCL if the composite score is lower than 0.

20. The method of claim 8, wherein the expression levels of CD10, MUM1, and FOXP1 are measured by an immunohistochemistry (IHC) method, and the percentage of the CD10 positively stained cells, the percentage of the MUM1 positively stained cells, and the percentage of the FOXP1 positively stained cells are determined by the IHC method.

21. The method of claim 8, wherein the composite score is determined according to: the composite score=(−1.4367173)+(−0.0238081×the CD10 percentage)+(0.01051371×the MUM1 percentage)+(0.02111138×the FOXP1 percentage).

22. The method of claim 8, wherein the method is used in combination with a second method for predicting if the subject has the ABC subtype of DLBCL or the non-ABC subtype of DLBCL.

23. The method of claim 8, wherein the subject has DLBCL the sample is obtained from a tissue of the subject comprising DLBCL cells.

24. The method of claim 8, wherein the treatment compound suitable for treating the ABC-subtype of DLBCL comprises lenalidomide or a stereoisomer or a mixture of stereoisomers, tautomer, pharmaceutically acceptable salt, solvate, isotopologue, prodrug, hydrate, co-crystal, clathrate, or a polymorph thereof.

* * * * *